(12) United States Patent
Boger et al.

(10) Patent No.: US 6,803,383 B2
(45) Date of Patent: Oct. 12, 2004

(54) INHIBITION OF ANGIOGENESIS AND TUMOR GROWTH

(75) Inventors: Dale L. Boger, La Jolla, CA (US); David A. Cheresh, Encinitas, CA (US)

(73) Assignee: The Scripps Research Institute, La Jolla, CA (US)

( * ) Notice: Subject to any disclaimer, the term of this patent is extended or adjusted under 35 U.S.C. 154(b) by 13 days.

(21) Appl. No.: 10/240,141

(22) PCT Filed: Mar. 27, 2001

(86) PCT No.: PCT/US01/09756

§ 371 (c)(1),
(2), (4) Date: Sep. 27, 2002

(87) PCT Pub. No.: WO01/72699

PCT Pub. Date: Oct. 4, 2001

(65) Prior Publication Data

US 2003/0083519 A1 May 1, 2003

Related U.S. Application Data

(60) Provisional application No. 60/192,260, filed on Mar. 27, 2000.

(51) Int. Cl.[7] .................. A01N 37/18; A01N 37/12; A01N 37/44; A61K 31/235; A61K 31/195
(52) U.S. Cl. .................. 514/542; 514/563; 514/619; 514/621; 560/32; 560/41; 560/159; 562/450; 564/167; 564/168; 564/47
(58) Field of Search .................. 514/542, 563, 514/619, 621; 560/32, 41, 159; 562/450; 564/167, 168, 47

(56) References Cited

U.S. PATENT DOCUMENTS

| | | | | |
|---|---|---|---|---|
| 5,747,514 A | * | 5/1998 | Beckett et al. | 514/352 |
| 5,840,939 A | * | 11/1998 | Beckett et al. | 554/37 |
| 5,872,152 A | * | 2/1999 | Brown et al. | 514/575 |

OTHER PUBLICATIONS

Kaskel et al, "Soluble p185/her2 and S100 in Yold Sac Blood from Human Melanoma Metastases Xenotransplanted to Chick Embryo" Anticancer Research, vol. 20(6D), pp. 5065–5068 (Nov.–Dec. 2000).*

* cited by examiner

Primary Examiner—Richard L. Raymond
Assistant Examiner—Zachary C. Tucker
(74) Attorney, Agent, or Firm—Olson & Hierl, Ltd.

(57) ABSTRACT

Compounds which inhibit tumor growth and angiogenesis, of general formula (II) are provided. These compounds include glycyl lysine derivatives bound to a central aromatic linking core.

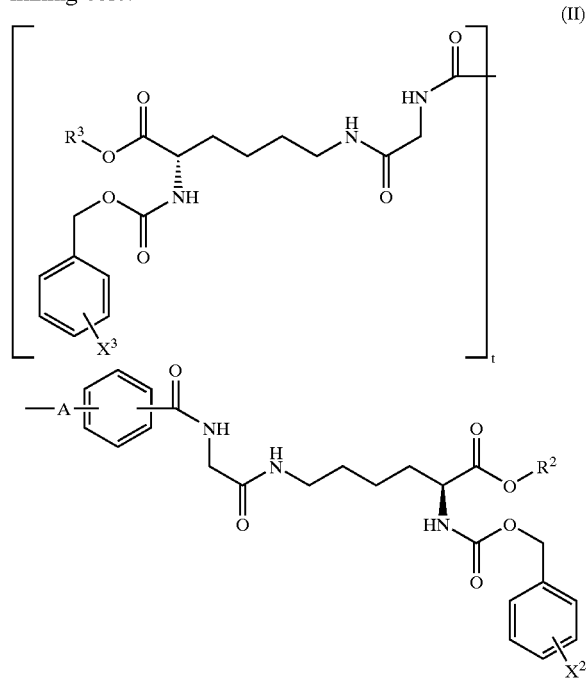

19 Claims, 5 Drawing Sheets

A

Compound 12    Compound 1    Control

B

C

INHIBITION OF ANGIOGENESIS AND TUMOR GROWTH

This application was filed under 35 U.S.C. 371, and is the U.S. national stage of PCT/US01/09756, filed March 2001 which claims benefit of 60/192,260 filed Mar. 27, 2000.

This invention was made with government support under Contract Nos. CA 78045, CA 45726, and CA 50286 by the National Institutes of Health. The United States Government has certain rights in this invention.

FIELD OF THE INVENTION

This invention relates to compositions for inhibiting angiogenesis and tumor growth. More particularly, the invention relates to compositions that bind to integrin $\alpha_v\beta_3$ and block the interaction of integrin $\alpha_v\beta_3$ with matrix metalloproteinase 2 (MMP2). The invention also relates to methods of inhibiting angiogenesis and tumor growth utilizing selective inhibitors of the binding of integrin $\alpha_v\beta_3$ with MMP2.

BACKGROUND OF THE INVENTION

Invasion of vascular cells into tissues requires the coordinated interplay of numerous factors including proteinases, which remodel the extracellular matrix architecture, as well as cell adhesion molecules that recognize this provisional matrix. Recent reports have implicated that the 72 kDa matrix metalloproteinase 2 (MMP2) is a key player in vascular development and angiogenesis. For example, Kitoh et al. (*J. Cell Sci.*, 109, 953–8 (1996)) report that MMP2 and its activator membrane type 1-matrix metalloproteinase (MT1-MMP) are coordinately expressed by mesenchymal cells almost exclusively during embryonic development, indicating specific matrix remodeling constraints in these tissues. In addition, angiogenesis and corresponding tumor growth are reduced in MMP2 knockout mice (see Itoh et al., *Cancer Res.*, 58 1048–51 (1998)). Interestingly, Saftor et al. (*Proc. Natl. Acad. Sci. U.S.A.*, 89, 1557–61 (1992)) have shown that ligation of the integrin $\alpha_v\beta_3$, itself a known mediator of angiogenesis, induces MMP2 production, suggesting a coordinated interplay of these two molecules during the vascular remodeling associated with blood vessel formation (see also Bafetti et al., *J. Biol. Chem.*, 273, 143–9 (1998)). In fact, direct interaction between MMP2 and integrin $\alpha_v\beta_3$ has been demonstrated by Brooks et al. (*Cell*, 85, 683–93 (1996)). The negative regulation of MMP2 during vascular invasion and maturation was later shown by Brooks et al. to be dependent upon expression of $\alpha_v\beta_3$ (*Cell*, 92, 391–400 (1998)).

Although inhibition of angiogenesis and concomitant suppression of tumor growth by natural as well as synthetic inhibitors of MMP's, including MMP2, has been documented, the translation of such strategies into clinical modalities has met with limited success, primarily due to the deleterious side effects of such broad spectrum inhibitors. Since MMP function, in general, may be required for many processes in the adult organism, active site inhibition of enzymatic function is likely to have far reaching effects on various biological processes involving tissue remodeling, such as wound healing. In fact, it has been documented that therapies with broad spectrum MMP inhibitors in clinical studies of various cancer types cause severe side effects, including inflammatory tendinitis, polyarthritis, and muscoskeletal pain syndromes, which are dose limiting and often persist after discontinuation of therapy. Given the limited distribution of integrin $\alpha_v\beta_3$ in adult organisms, however, one would predict that targeting the interaction between MMP2 and $\alpha_v\beta_3$ to the areas of neovascularization or cellular invasion should correspondingly limit the effects of such treatment-related toxicities. Indeed, the recombinant non-catalytic carboxy-terminal hemopexin domain of MMP2 (PEX), which mediates MMP2 binding to integrin $\alpha_v\beta_3$, has shown antiangiogenic and antitumor activity in vivo. The potential utility of such a large protein fragment, but with attendant shortcomings (e.g. large scale production problems, FDA quality and safety control issues and antigenicity), suggested the need for a more practical solution to this problem.

There is a need therefore, for chemical compounds that selectively inhibit MMP activity at tumor growth sites with minimal inhibition of MMP in other regions of the body.

SUMMARY OF THE INVENTION

The present invention provides novel compounds useful as inhibitors of angiogenesis and tumor growth. The invention also provides a method for the inhibition of the interaction of MMP2 with integrin $\alpha_v\beta_3$ and a method for inhibition of angiogenesis in cells containing integrin $\alpha_v\beta_3$. Further, the invention provides a method for inhibition of tumor growth by administration of MMP2-$\alpha_v\beta_3$ interaction inhibitors.

The compounds of the present invention are represented by Formula (I) and include glycyl lysine derivatives chemically attached to a linking group:

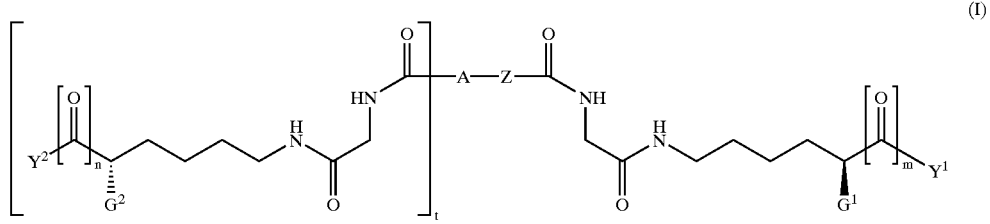

(I)

wherein $G^1$ and $G^2$ are each independently —NH—C(O)—O—$R^1$, —NH—C(O)—O—$(CH_2)_v$—$(C_6H_4)$—$X^1$, —NH—C(O)—NH—$(CH_2)_v$—$(C_6H_4)$—$X^1$, —O—C(O)—NH—$(CH_2)_v$—$(C_6H_4)$—$X^1$, —O—C(O)—O—$(CH_2)_v$—$(C_6H_4)$—$X^1$, or —NH—C(O)—$CH_2$—$(C_6H_4)$—$X^1$; $Y^1$ and $Y^2$ are each independently OH, $C_1$–$C_4$ alkyl, $C_1$–$C_4$ hydroxyalkyl, $C_1$–$C_4$ alkoxy, phenyl, benzyl, or —$NH_2$; $R^1$ is $C_1$–$C_4$ alkyl; $X^1$ is halo, nitro, $C_1$–$C_4$ alkyl, $C_1$–$C_4$ alkoxy, or $C_1$–$C_4$ perfluoroalkyl; Z is —C≡C—, —$C_6H_4$—, cis —CH=CH—, trans —CH=CH—, cis —$CH_2$—CH=CH—$CH_2$—, trans —$CH_2$—CH=CH—$CH_2$—, 1,4-naphthyl, cis-1,3-cyclohexyl, trans-1,3-cyclohexyl, cis-1,4-cyclohexyl, or trans-1,4-cyclohexyl; A is H or a covalent bond; m and n are each independently an integer having a value of 0 or 1; t is an integer having a value of 0 or 1; and v is an integer having a value of 1 or 2; with provisos that when A is H, t is 0; when A is a covalent bond, t is 1; when m is 0, $Y^1$ is $C_1$–$C_4$ hydroxyalkyl; and when n is 0, $Y^2$ is $C_1$–$C_4$ hydroxyalkyl. These compounds bind to $\alpha_v\beta_3$ and inhibit the interaction of MMP2 with $\alpha_v\beta_3$.

Preferred compounds of structural Formula (I) are represented in structural Formula (II):

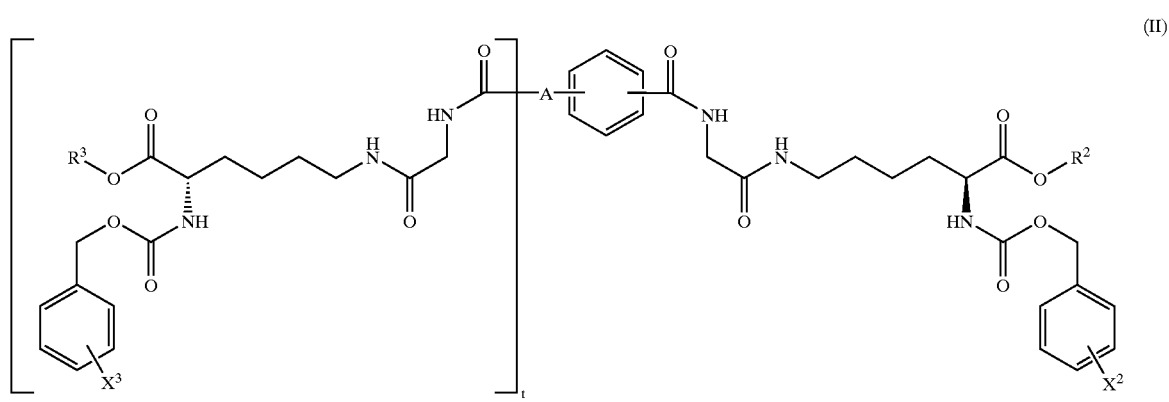

(II)

wherein $R^2$ and $R^3$ are each independently H, $C_1$–$C_4$ alkyl, phenyl or benzyl; $X^2$ and $X^3$ are each independently halo, nitro, $C_1$–$C_4$ alkoxy, $C_1$–$C_4$ alkyl, or $C_1$–$C_4$ perfluoroalkyl; A is H or a covalent bond; and t is an integer having a value of 0 or 1; with the proviso that when A is H, t is 0 and when A is a covalent bond, t is 1. When A is a covalent bond and t is 1, the glycyl lysine derivative moieties may be attached to the benzene linking group in the ortho, meta or para position.

When compounds of Formulas (I) and (II) are administered to cells containing $\alpha_v\beta_3$, the binding of $\alpha_v\beta_3$ with MMP2 is inhibited, thus interfering with an essential mechanism in angiogenesis. Interference with angiogenesis can also inhibit tumor growth by preventing vascularization of the tumor, thus starving it of nutrition. The angiogenesis and tumor growth inhibiting compounds of the present invention are thus useful therapeutic agents for the treatment of patients with tumors or angiogenic disorders. Because the present compounds bind to $\alpha_v\beta_3$, these compounds can also be used to suppress inflammatory events.

The compounds of the present invention may be formulated in suitable pharmaceutically acceptable media to afford pharmaceutical compositions useful for the treatment of tumors and other disorders involving undesired angiogenesis.

In a method aspect of the present invention, pharmaceutical compositions containing the compounds of Formulas (I) and (II) are prepared by formulating the compound in a pharmaceutically acceptable matrix. The pharmaceutical compositions of the active compounds are administered to a patient with a tumor to reduce or eliminate tumor growth. The active compounds can be administered parenterally by injection or by gradual infusion over time, or by any other method suitable for the particular dosage form.

BRIEF DESCRIPTION OF THE DRAWINGS

In the accompanying drawings:

FIG. 5D is a microscopic depiction of tumor cell density in Chick CAM tissue.

DETAILED DESCRIPTION OF THE INVENTION

Figure 1:
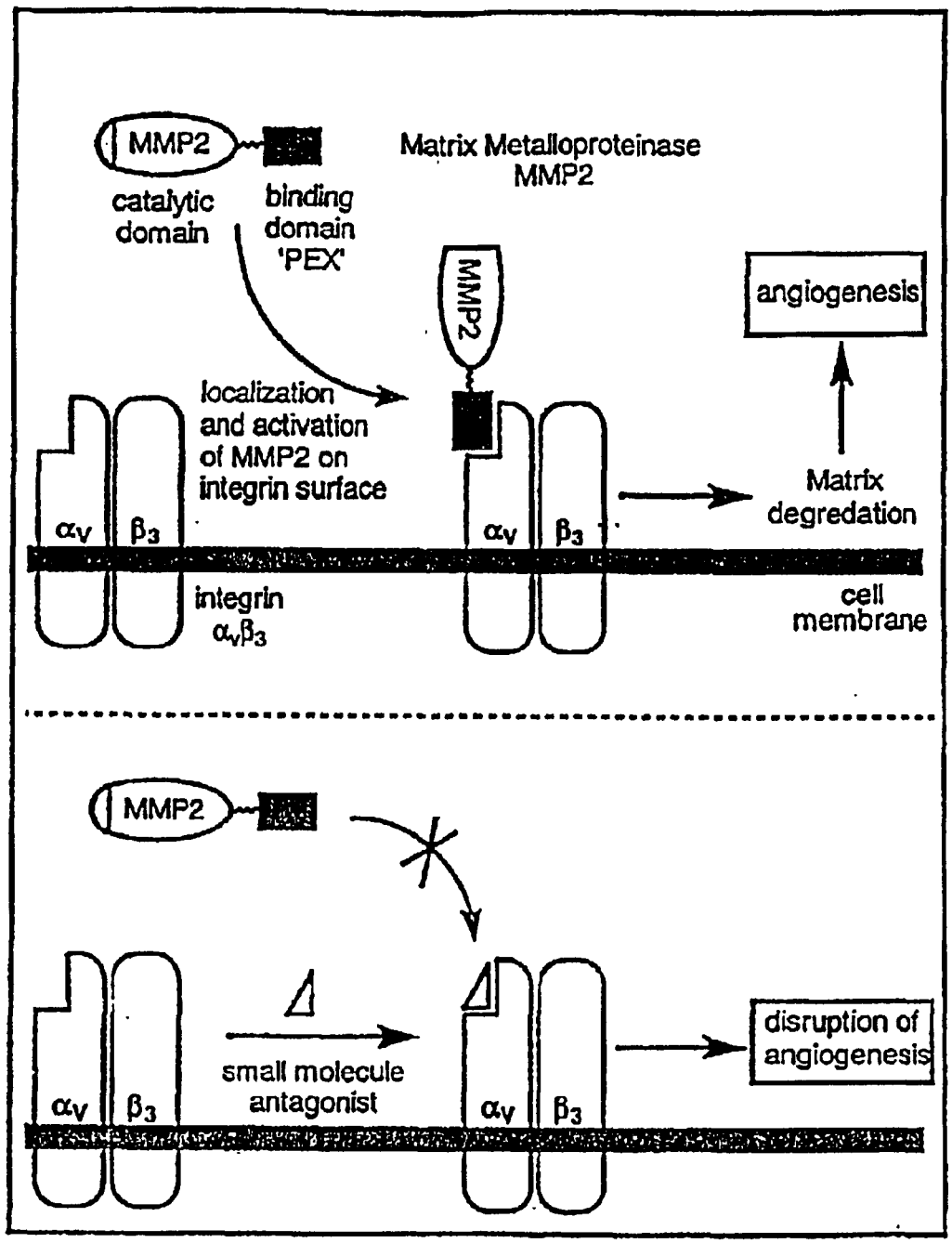
FIG. 1 is a schematic illustration depicting MMP2 interaction with integrin $\alpha_v\beta_3$ and its role in angiogenesis as well as the inhibition of MMP2 interaction with $\alpha_v\beta_3$ by an antagonist such as the compounds of the present invention.

The binding of MMP2 to integrin $\alpha_v\beta_3$ is an important mechanism in the process of angiogenesis. Specific inhibition of this binding interaction results in a reduction in vascularization in growing tissues such as tumors, and thus retards tumor growth. The interaction of MMP2 with integrin $\alpha_v\beta_3$ is illustrated pictorially in FIG. 1. A new class of angiogenesis and tumor growth inhibitors, are small molecule antagonists described below, that specifically interfere with the binding of MMP2 to integrin $\alpha_v\beta_3$ thus affording an important new treatment tool.

Certain compounds of this invention may possess one or more asymmetric centers and may exist in optically active forms. Additional asymmetric centers may be present in a substituent group, such as an alkyl group. Pure S-isomers and pure R-isomers, racemic mixtures of the isomers, and mixtures thereof are intended to be within the scope of this invention. Chiral forms of certain compounds of this invention are contemplated, and are specifically included within the scope of this invention.

The term "alkoxy" means an oxygen atom linked by an ether bond to an alkyl group, as defined below, of the size indicated. Examples of alkoxy groups are methoxy, ethoxy, t-butoxy, and the like. The term "alkyl" means a straight- or branched-chain carbon radical of the size indicated. Representative of alkyl radicals are methyl, ethyl, n-propyl, isopropyl, n-butyl, sec-butyl, isobutyl, t-butyl, 2-ethylhexyl, n-octyl, 2,4-dimethylpentyl, and the like. The term "hydroxyalkyl" means an alkyl group, as defined above, of the size indicated, attached to a hydroxyl group. Examples include hydroxymethyl, 2-hydroxyethyl, 3-hydroxy-1-propyl, 2-hydroxy-1-propyl, 4-hydroxybutyl, and the like.

The term "perfluoroalkyl" refers to a allkyl group of the size indicated, as defined below, bearing fluoro substituents in place of each hydrogen, for example trifluoromethyl and pentafluoroethyl.

The terms "halo" or "halogen" refer to bromo, chloro, fluoro and iodo.

The compounds of the present invention are represented by Formula (I) and include glycyl lysine derivatives chemically attached to a linking group:

$(C_6H_4)$—$X^1$, or —NH—C(O)—$CH_2$—$(C_6H_4)$—$X^1$; $Y^1$ and $Y^2$ are each independently OH, $C_1$–$C_4$ alkyl, $C_1$–$C_4$ hydroxyalkyl, $C_1$–$C_4$ alkoxy, phenyl, benzyl, or —$NH_2$; $R^1$ is $C_1$–$C_4$ alkyl; $X^1$ is halo, nitro, $C_1$–$C_4$ alkyl, $C_1$–$C_4$ alkoxy, or $C_1$–$C_4$ perfluoroalkyl; Z is —C≡C—, —$C_6H_4$—, cis —CH=CH—, trans —CH=CH—, cis —$CH_2$—CH=CH—$CH_2$—, trans —$CH_2$—CH=CH—$CH_2$—, 1,4-naphthyl, cis-1,3-cyclohexyl, trans-1,3-cyclohexyl, cis-1,4-cyclohexyl, or trans-1,4-cyclohexyl; A is H or a covalent bond; m and n are each independently an integer having a value of 0 or 1; t is an integer having a value of 0 or 1; and v is an integer having a value of 1 or 2; with provisos that when A is H, t is 0; when A is a covalent bond, t is 1; when m is 0, $Y^1$ is $C_1$–$C_4$ hydroxyalkyl; and when n is 0, $Y^2$ is $C_1$–$C_4$ hydroxyalkyl.

Preferably $G^1$ and $G^2$ are —NH—C(O)—O—$(CH_2)_v$—$(C_6H_4)$—$X^1$, $Y^1$ and $Y^2$ are OH, and m and n are 1. Preferably, $X^1$ is $C_1$–$C_4$ perfluroalkyl, most preferably trifluoromethyl. Preferred compounds within the purview of structural Formula (I) are represented in structural Formula (II) and include glycyl lysine derivatives attached to a benzene linking group in either the ortho, meta or para orientation:

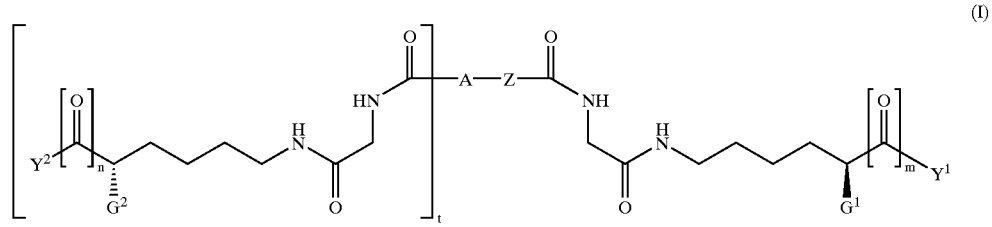

(I)

wherein $G^1$ and $G^2$ are each independently —NH—C(O)—O—$R^1$, —NH—C(O)—O—$(CH_2)_v$—$(C_6H_4)$—$X^1$, —NH—C(O)—NH—$(CH_2)_v$—$(C_6H_4)$—$X^1$, —O—C(O)—NH—$(CH_2)_v$—$(C_6H_4)$—$X^1$, —O—C(O)—O—$(CH_2)_v$—

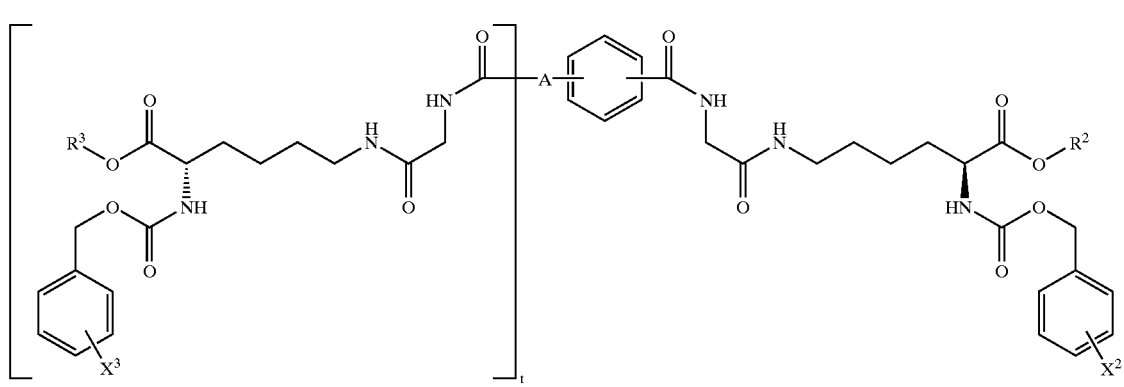

(II)

wherein $R^2$ and $R^3$ are each independently H, $C_1$–$C_4$ alkyl, phenyl or benzyl; $X^2$ and $X^3$ are each independently halo, nitro, $C_1$–$C_4$ alkoxy, $C_1$–$C_4$ alkyl, or $C_1$–$C_4$ perfluoroalkyl; A is H or a covalent bond; and t is an integer having a value of 0 or 1; with the proviso that when A is H, t is 0 and when A is a covalent bond, t is 1. When A is a covalent bond and t is 1, the glycyl lysine derivative moieties may be attached to the benzene linking group in the ortho, meta or para position.

Preferably, the substituents $X^2$ and $X^3$ are attached to the phenyl ring of the benzyl moiety in the 4-position relative to the benzylic $CH_2$ (i.e. para substituent). The preferred $X^2$ and $X^3$ groups are $C_1$ to $C_4$ perfluoroalkyl, most preferred is para-trifluoromethyl. The preferred $R^2$ and $R^3$ groups are hydrogen and methyl. The substituents $X^2$ and $X^3$ may be the same or different, and the substituents $R^2$ and $R^3$ may also be the same or different.

A particularly active member of the family of compounds represented by Formula (II), wherein A is a covalent bond and t is 1, is the compound represented by Compound 1 below:

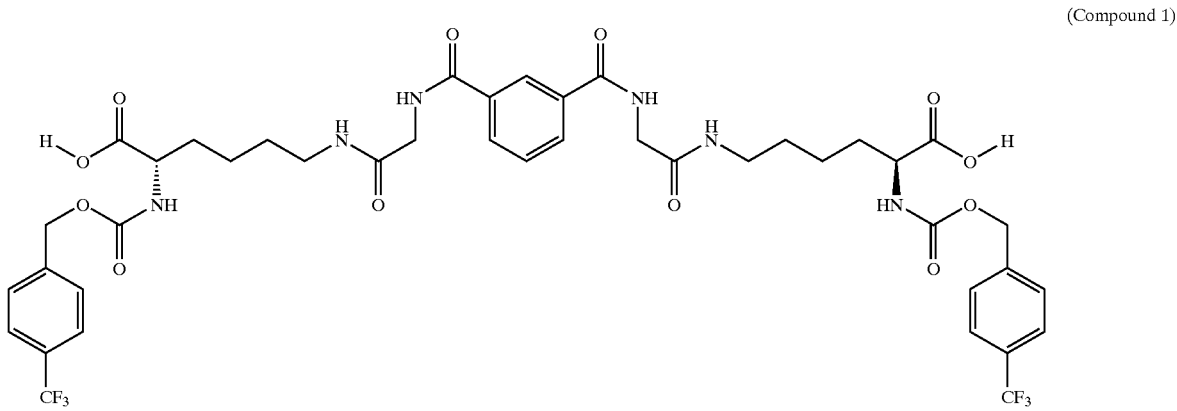

(Compound 1)

The compounds of Formulas (I) and (II) may be synthesized from readily available materials in a moderate number of synthetic steps. For example, Scheme 1 shows the synthesis of Compound 1, and is illustrative of a general method of producing compounds of Formula (II) wherein A is covalent bond, $R^2$ and $R^3$ are the same and $X^2$ and $X^3$ are the same. Scheme 1 further illustrates the synthesis of compounds of Formula (II), wherein $X^2$ and $X^3$ are both para-trifluoromethyl, and $R^2$ and $R^3$ are both either methyl or hydrogen.

Scheme 1.

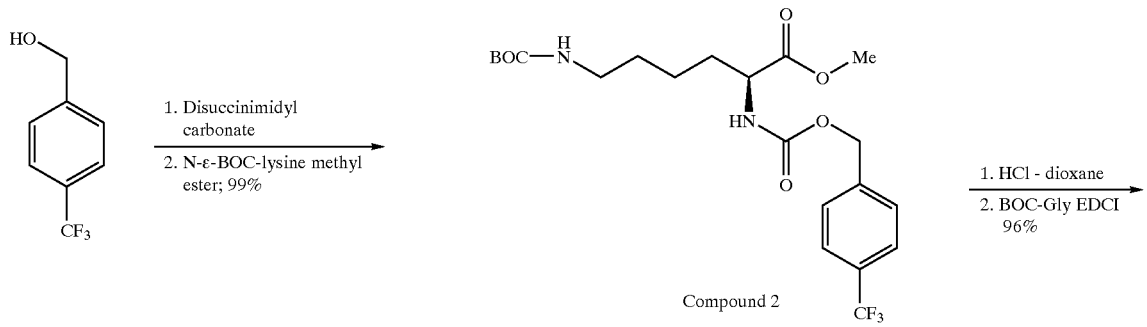

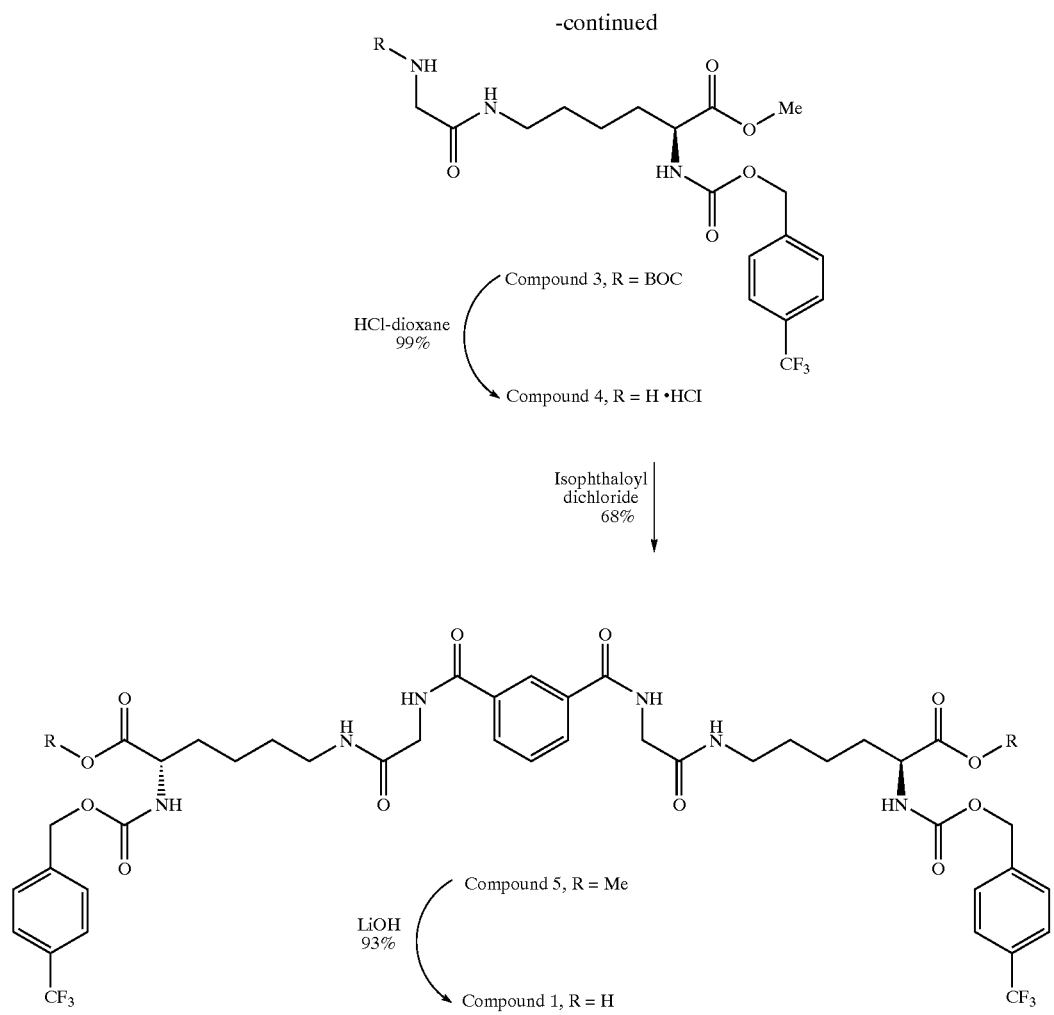

Compound 3, R = BOC
HCl-dioxane 99%
Compound 4, R = H •HCl

Isophthaloyl dichloride 68%

Compound 5, R = Me
LiOH 93%
Compound 1, R = H

[$^{14}$C]-Compound 1 was prepared in 25% overall yield from BOC-[$^{14}$C]-Gly

In Scheme 1, p-trifluoromethyl benzyl alcohol was reacted with disuccinimidyl carbonate to form an activated ester intermediate, which, in turn, was reacted with N-ε-BOC-lysine methyl ester to afford Compound 2 in 99% yield. Hydrolysis of the BOC protecting group and subsequent coupling with BOC-glycine afforded Compound 3 in 96% yield. Acid hydrolysis of the BOC protecting group of Compound 3 afforded Compound 4 in 99% yield. Coupling of two equivalents of Compound 4 with isophthaloyl dichloride provided a 68% yield of Compound 5, corresponding to Formula (II) where $R^2$ and $R^3$ are methyl, $X^2$ and $X^3$ are p-trifluoromethyl, and A is a covalent bond. Hydrolysis of Compound 5 with lithium hydroxide produced a 93% yield of Compound 1.

The syntheses of compounds of Formulas (I) and (II) that are analogs of Compound 1 having other R and X substituents may be achieved by modifications of Scheme 1 that will be readily apparent to those of skill in the synthetic chemical arts. Use of a benzyl alcohol with a substituent other than p-trifluoromethyl (e.g. halo, nitro or other $C_1$ to $C_4$ perfluoroalkyl groups in either the ortho, meta or para position relative to the benzyl $CH_2$) or use of a protected lysine ester having an ester group other than methyl, will afford other compounds of Formula (II).

The synthesis of compounds of Formula (I) having Z groups other than 1,3-phenyl is achieved, for example, by the substitution of other diacid dichlorides, such as bischlorocarbonylacetylene, fumaryl dichloride, phthaloyl dichloride, for isophthaloyl dichloride in Scheme 1. Alternativelyl, the corresponding acids may be utilized in the place of the acid chlorides, and coupling of the acids to the appropriate amines may be achieved via standard peptide coupling techniques well known in the art. Those of skill in the art will readily recognize other chemical material substitutions that can be made in the synthetic methods illustrated in Schemes 1 and 2 to synthesize other members of the group of compounds represented in Formulas (I) and (II). The synthesis of related compounds and useful chemical strategies adaptable to the synthesis of compounds of Formulas (I) and (II) are described by Boger et al. in *J. Am. Chem. Soc.* 123, 1280–1288 (2001).

Compounds of Formula (II) wherein A is a covalent bond, t is 1 and either $R^2$ is different from $R^3$, or $X^2$ is different from $X^3$, or both $R^2/R^3$ and $X^2/X^3$ differ, can also be synthesized by modifications of the method presented in Scheme 1, which will be readily apparent to those of skill in the art. For example, one equivalent of Compound 4 can be reacted with the isophthaloyl dichloride, or any suitable isophthalic halide or active ester, and the second activated acid group can be sequentially reacted with an analog of Compound 4 having either a different X group, or a different R group, or both. Likewise, two analogs of Compound 4 having either a different X groups, or a different R group, or both can be sequentially reacted with isophthaloyl dichloride or an equivalent activated isophthalate to provide additional analogs of Compound 1 with dissimilar X and R groups.

The synthesis of compounds of Formula (II), wherein A is hydrogen and t is 0 is illustrated by the synthesis of Compounds 6 and 7 in Scheme 2, below:

Scheme 2

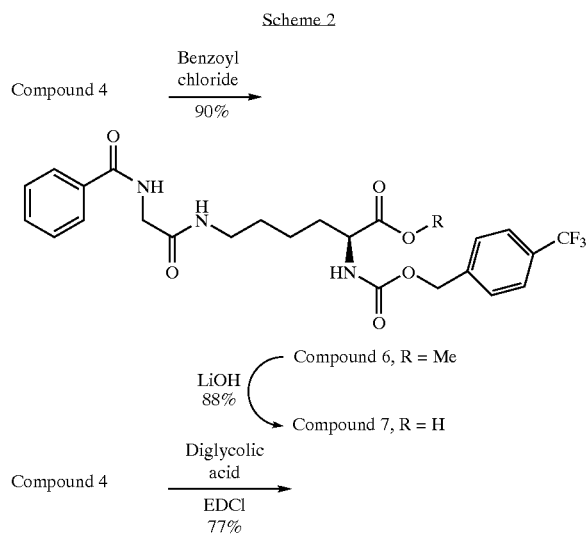

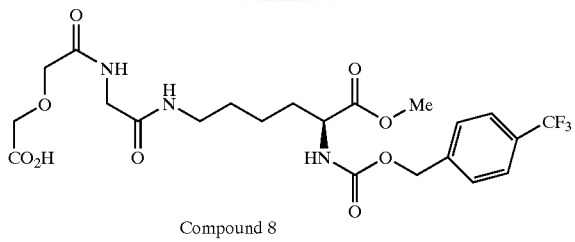

Compound 8

In Scheme 2, Compound 4 of Scheme 1 is reacted with benzoyl chloride to afford Compound 6 ($R^2$=methyl; $X^2$=p-trifluoromethyl) in 90% yield. Hydrolysis of the ester group of 6 with lithium hydroxide afforded Compound 7 ($R^2$=H, $X^2$=p-trifluoromethyl) in 88% yield.

Benzoylation of analogs of Compound 4 with different R groups (e.g. other $C_1$–$C_4$ alkyl groups) and/or with different X substituents on the benzyl group lead to other compounds of Formula (II) having A=H and t=0.

Also illustrated in Scheme 2 is the synthesis of Compound 8, an inactive analog of Compounds 6 and 7 wherein the benzoyl moiety attached to the glycine unit of Formula (II) is replaced by a diglycolic amide group. Compound 9 is obtained in 77% yield by coupling of Compound 4 to diglycolic acid.

Scheme 3, below, illustrates the synthesis of Compound 12, an inactive analog of Compound 1, in which the p-trifluoromethylbenzyloxycarbonyl group of Formula (II) is replaced by a benzoyl amide.

Scheme 3.

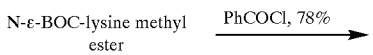

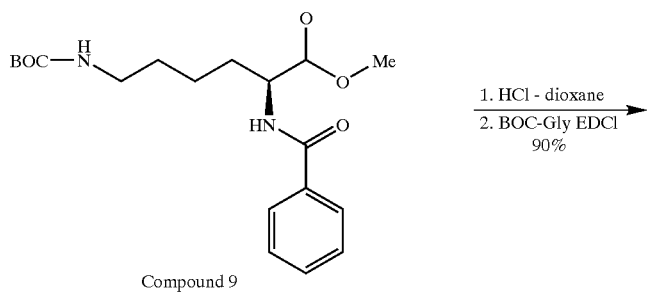

Compound 9

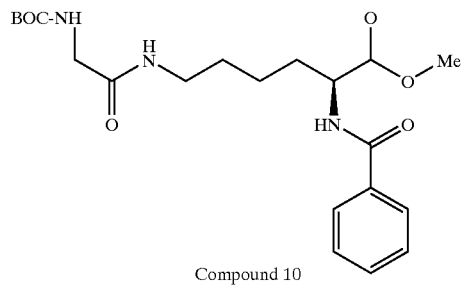

Compound 10

-continued

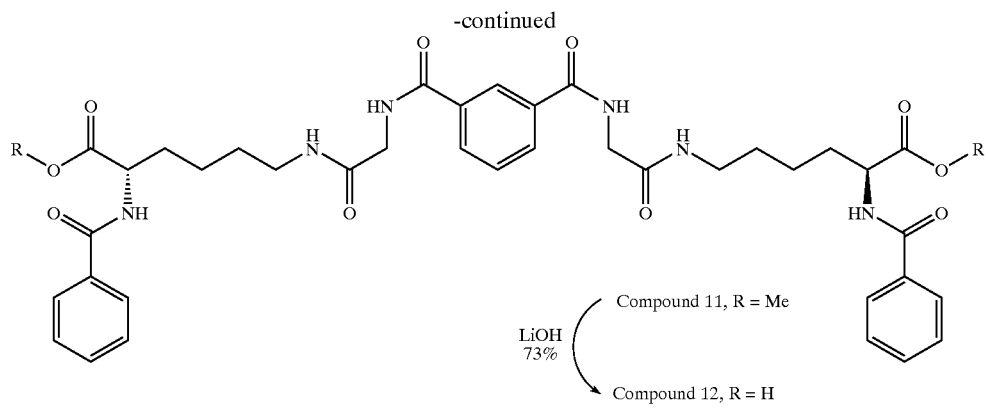

In a method aspect of the present invention, pharmaceutical preparations of compounds of Formulas (I) and (II) can be prepared by formulating the compound in a pharmaceutically acceptable carrier matrix. The pharmaceutical compositions comprising the active compounds of Formulas (I) and (II) are administered to a host with a tumor to reduce or eliminate tumor growth. The active compounds can be administered parenterally by injection, or by gradual infusion over time. Although the tissue to be treated is most often treated by intraperitoneal or subcutaneous administration, the active compounds can also be administered intraocularly, intravenously, intramuscularly, intrasynovially, intracavity, or transdermally, and can be delivered by peristaltic means as well.

The term "administration" of the inventive compound or composition, as used herein, refers to systemic use as when taken orally, parenterally, by inhalation spray, by nasal, rectal or buccal routes, or topically in dosage form unit formulations containing conventional nontoxic pharmaceutically acceptable carriers, adjuvants and vehicles as desired. The term "parenteral" as used herein includes intravenous, intramuscular, intraperitoneal, intrasternal, subcutaneous and intraarticular injection and infusion techniques.

By "pharmaceutically acceptable" it is meant those salts, amides and esters which are, within the scope of sound medical judgement, suitable for use in contact with the tissues of humans and lower animals without undue toxicity, irritation, allergic response and the like, and are commensurate with a reasonable benefit/risk ratio, effective for their intended use in the treatment of tumors and angiogenic-related disorders.

Pharmaceutically acceptable salts are well known in the art. For example, S. M Berge, et al. describe pharmaceutically acceptable salts in detail in *J. Pharmaceutical Sciences*, 66: 1–19 (1977). Representative acid addition salts include hydrochloride, hydrobromide, sulfate, bisulfate, acetate, oxalate, valerate, oleate, palmitate, stearate, laurate, borate, benzoate, lactate, phosphate, toluenesulfonate, methanesulfonate, citrate, maleate, fumarate, succinate, tartrate, ascorbate, glucoheptonate, lactobionate, lauryl sulfate salts and the like. Representative alkali or alkaline earth metal salts include sodium, calcium, potassium, magnesium salts and the like.

As used herein, the term "pharmaceutically acceptable carriers" means a non-toxic, inert solid, semi-solid or liquid filler, diluent, encapsulating material or formulation auxiliary of any type. Some examples of the materials that can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator. Examples of pharmaceutically acceptable antioxidants include water soluble antioxidants such as ascorbic acid, cysteine hydrochloride, sodium bisulfite, sodium metabisulfite, sodium sulfite, and the like; oil soluble antioxidants such as ascorbyl palmitate, butylated hydroxyanisole (BHA), butylated hydroxytoluene (BHT), lecithin, propyl gallate, alpha-tocopherol and the like; and the metal chelating agents such as citric acid, ethylenediamine tetraacetic acid (EDTA), sorbitol, tartaric acid, phosphoric acid and the like.

By a "therapeutically effective amount" of the inventive agent or compound is meant a sufficient amount of the compound to treat tumors and angiogenic-related disorders at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidently with the specific compound employed; and like factors well known in the medical arts.

This invention also provides pharmaceutical compositions in unit dosage forms, comprising a therapeutically effective amount of a compound (or compounds) of this invention in combination with a conventional pharmaceutical carrier. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides.

In addition, fatty acids such as oleic acid are used in the preparation of injectables. The injectable formulation can be sterilized, for example, by filtration through a bacteria-retaining filter, or by incorporating sterilizing agents in the form of sterile solid compositions which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions which are compatible with body tissues.

Suppositories for rectal administration of the drug can be prepared by mixing the drug with a suitable nonirritating excipient such as cocoa butter and polyethylene glycol which are solid at ordinary temperature but liquid at the rectal temperature and will therefore melt in the rectum and release the drug.

Solid dosage forms for oral administration may include capsules, tablets, pills, powders, prills and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings. Solid compositions of a similar type may also be employed as fillers in soft and hard-filled gelatin capsules using such excipients as lactose or milk sugar as well as high molecular weight polyethylene glycols and the like.

Liquid dosage forms for oral administration may include pharmaceutically acceptable lo emulsions, microemulsions, solutions, suspensions, syrups and elixirs containing inert diluents commonly used in the art such as water. Such compositions may also comprise adjuvants, such as wetting agents; emulsifying and suspending agents; sweetening, flavoring and perfuming agents. If desired, the compounds of the present invention can be incorporated into slow release or targeted delivery systems such as polymer matrices, liposomes and microspheres. They may be sterilized, for example, by filtration through a bacteria-retaining filter, or by incorporating sterilizing agents in the form of sterile solid compositions which can dissolve in sterile water, or some other sterile injectable medium immediately before use. The active compounds can also be in micro-encapsulated form with one or more excipients as noted above.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes. Dosage forms for topical or transdermal administration of a compound of this invention further include ointments, pastes, creams, lotions, gels, powders, solutions, sprays, inhalants or patches. The active component is admixed under sterile conditions with a pharmaceutically acceptable carrier and any needed preservatives or buffers as may be required.

Ophthalmic formulations, ear drops, eye ointments, powders and solutions are also contemplated as being within the scope of this invention. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

The compositions containing the active compounds are administered in a manner compatible with the dosage formulation and in a therapeutically effective amount. The quantity to be administered and the timing of administration depend on the host to be treated, capacity of the host's system to utilize the active ingredient, and degree of therapeutic effect desired. Precise amounts of the active ingredient required to be administered depend on the judgment of the practitioner, and are peculiar to each individual.

Suitable dosage ranges for systemic application are disclosed herein and depend on the route of administration. Suitable regimes for administration are also variable, but are typified by an initial administration, followed by repeated doses at one or more predetermined intervals by a subsequent injection or other route of administration.

The present invention also provides a pharmaceutical composition useful for practicing the therapeutic methods described herein. The compositions contain an active compound described hereinabove, together with a pharmaceutically acceptable carrier.

Preparations for parental administration of the present compounds or compositions include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parental vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present, such as, for example, antimicrobials, antioxidants, chelating agents, inert gases, and the like.

Another aspect of the present invention provides a method for inhibiting MMP2 interaction with $\alpha_v\beta_3$ and thus angiogenesis in a tumor tissue. The inhibiting method comprises administering to the host a composition comprising an angiogenesis-inhibiting amount of a compound described hereinabove. MMP2 interaction with $\alpha_v\beta_3$ is inhibited by contacting $\alpha_v\beta_3$ with a compound of the present invention.

Angiogenesis is the formation of a neovascular network from pre-existing host vessels and is required for tumor growth beyond 1–2 mm$^3$. For the purpose of the present invention, angiogenesis is inhibited as long as angiogenesis and the disease symptoms mediated by angiogenesis are ameliorated.

The dosage ranges for the administration to a host of the active compound depend upon the particular active compound and its potency to a particular tumor or integrin. One skilled in the art can readily determine the proper dosage for a particular active compound without undue experimentation. The host can be any mammal. The dosage should be large enough to produce the desired therapeutic effect in which angiogenesis and the disease symptoms mediated by angiogenesis are ameliorated, and is usually an amount sufficient to maintain a plasma level of the active compound in the range of about 0.01 to about 100 micromolar ($\mu$M), preferably about 0.2 to about 20 $\mu$M, more preferably about 1 to about 10 $\mu$M. The dosage should not be so large as to cause adverse side effects, however. The dosage per kilogram (kg) of body weight can vary from 1 to 20 mg per dose, in one or more dose administrations daily, for one or several days or indefinitely.

For inhibition of angiogenesis, the therapeutically effective amount is an amount of active compound sufficient to produce a measurable inhibition of angiogenesis in the tissue being treated, i.e., an angiogenesis-inhibiting amount or an MMP2-$\alpha_v\beta_3$ interaction inhibiting amount. Inhibition of angiogenesis can be measured in situ by immunohistochemistry, as described herein, or by other methods known to one skilled in the art.

The present invention additionally provides pharmaceutical compositions useful for practicing the therapeutic methods described herein. The compositions contain an active compound defined hereinabove together pharmaceutically acceptable carrier.

The present invention also provides a method of inducing apoptosis in tumor cells. This method comprises administering to the host a therapeutically effective amount of an active compound sufficient to initiate tumor cell apoptosis.

For the purpose of the present invention, tumor cell apoptosis is induced if an increased tumor cell apoptosis is observed in the target tumor being treated. Tumor cell apoptosis can be measured by methods described herein or commonly known in the art.

The following non-limiting examples are provided to illustrate various aspects of the present invention.

Materials and Methods

Antibodies Cells and Reagents. CS-1 hamster melanoma cells and CS-1 cells transfected with the human $\beta_3$-integrin subunit ($\beta_3$CS-1 cells) were described previously (*Cell*, 85, 683–93 (1996); *Cell*, 92, 391–400 (1998)). The horseradish peroxidase (HRP)-conjugated monoclonal antibodies anti-biotin mAb BN-34 and anti-actin mAb AC-40 were obtained from Sigma (St. Louis, Mo.). Anti-von Willebrand Factor (vWF) polyclonal antibodies (pAb) were obtained from DAKO (Glostrup, Denmark). The cyclic peptides cRGDfV and cRADfV and integrin-$\alpha_v\beta_3$ were generously provided by Merck KGaA (Darmstadt, Germany). Purified proMMP2 and integrin-$\alpha_v\beta_3$ were provided by Chemicon International (Temecula, Calif.). Purified active MMP2 was obtained from Calbiochem (La Jolla, Calif.). Basic fibroblast growth factor (bFGF) was kindly provided by Scios (Mountain View, Calif.).

Synthesis [$^{14}$C]-Compounds. [$^{14}$C]-labeled Compound 1 was synthesized by a slight modification of the sequence described earlier for the unlabeled material (Scheme 1), but utilizing N-BOC-[1-$^{14}$C]-glycine (55 mCi/mmol, American Radiolabeled Chemicals, St. Louis, Mo.). The overall yield of [$^{14}$C]-Compound 1 was 25% for the four step sequence.

EXAMPLE 1

Solid Phase Integrin Binding Assays

Purified integrins were adsorbed overnight onto microtiter wells (1–5 $\mu$g/ml, 50 $\mu$g/well) prior to blocking with Casein-blocker (Pierce, Rockford, Ill.). Purified biotinylated MMP2 (bMMP2, 3–5 nM) in binding buffer (50 mM Tris, pH 8, 150 mM NaCl, 1 mM MgCl$_2$, 0.5 mM MnCl$_2$) was added to the wells in the presence or absence of Compound 1, Compound 12, cyclic RGD or RAD peptides, or buffer vehicle alone. Control wells received no integrin. Biotinylated vitronectin (bVN, 1 $\mu$g/ml) was used as a reference. Bound protein was detected with HRP-anti-biotin mAb and quantitated at 450 nm with 3,3',5,5'-tetramethylbenzidine solution (TMB; a substrate for the peroxidase) (BioRad, Hercules, Calif.).

For the assessment of direct integrin binding by Compound 1, $\alpha_v\beta_3$ and $\alpha_5\beta_1$ (10 $\mu$g/ml, 50 $\mu$l/well) were coated onto Immulon-4 microtiter wells (Dynatech Laboratories, Chantilly, Va.), which were substantially blocked and incubated with titration of [$^{14}$C]-Compound 1 prior to the addition of 150 $\mu$l of binding buffer containing 0.1% Tween-20 and aspiration of all liquid. Dried wells were separated and immersed in BetaMax liquid scintillation cocktail (ICN Biochemicals, Costa Mesa, Calif.) for quantitation. From this binding curve a subsaturating concentration (3 $\mu$M) of [$^{14}$C]-Compound 1 was examined in the presence and absence of a 25-fold molar excess (75 $\mu$l) of unlabeled Compound 1 or Compound 12, or 100 $\mu$M cyclic RGD or RAD peptide. Control was bVN, used and detected as described above.

EXAMPLE 2
MMP2 Cell-Binding and [$^3$H]-Collagen IV Degradation Assays

CS-1 cells or $\beta_3$CS-1 cells were incubated in adhesion buffer fibroblast basal medium (FBM) supplemented with 0.5% bovine serum albumin (BSA), 0.4 mM $MnCl_2$ and 10 μg/ml aprotinin) containing either 4 nM purified active MMP2 alone, or in combination with 10 μM Compound 1 or Compound 12 for 45 minutes at 37° C. prior to washing and addition to the [$^3$H]-collagen IV-coated wells. Wells had been coated overnight with 50 μl of 0.414 mCi/ml [$^3$H]-collagen IV (ICN Biochemicals, Costa Mesa, Calif.) and washed extensively until the radioactivity in the recovered wash solution reached background. Alternatively, cells were treated as above in the absence of MMP2, or the MMP2 solutions were added directly to the wells without cells, as controls. Collagen IV degradation was quantitated by measuring the radioactivity released into the 50 μl of culture medium as determined in a liquid scintillation counter. For the assessment of biotinylated MMP2 binding to CS-1 cells, cells were suspended in adhesion buffer and incubated with 12 nM bMMP2 for 45 minutes at 37° C. in the presence or absence of 10 μM Compound 1 or Compound 12. Cells were subsequently washed before lysis and processing for SDS-PAGE and immunoblotting with an anti-biotin mAb.

EXAMPLE 3
Chick Chorioallontoic Membrane (CAM) Angiogenesis Assay

Angiogenesis was assessed essentially as described previously (*Cell*, 85, 683–93 (1996); *Cell*, 92, 391–400 (1998)). After stimulation with 3 μg/ml of basic fibroblast growth factor (bFGF), 10 day chick embryo CAMs were treated with 20 μl of 3 μM Compound 1 or Compound 12. Three days after induction, the CAMs were quantitated in a blind evaluation. CAMs from each group were pooled, minced, and extracted with 50 mM Tris, 150 nM NaCl, 0.1% Triton X-100 containing COMPLETE-brand protease inhibitor cocktail without EDTA (Boehringer, Mannheim, Germany) prior to analysis by zymography.

EXAMPLE 4
SDS-PAGE, Immunoblotting and Zymography

Immunoblotting. Equal quantities of protein were separated by SDS-PAGE under reducing conditions and electroblotted to an Immobilon-P membrane (Millipore, Bedford, Md.). The membrane was blocked and immobilized proteins were detected by incubation with an antigen-specific primary antibody, followed by an HRP-conjugated secondary antibody as required. Bands were visualized the chemiluminescent substrate PS-3 (Lumigen, Inc., Southfield, Mich.).

Zymography. Chick CAM lysates were prepared as described above and equal quantities of protein were separated in the absence of reducing agents or boiling on polyacrylamide gels embedded with 0.2% gelatin. The gels were washed with 2% Triton X-100, followed by extensive washing with water prior to overnight incubation at 37° C. in collagenase buffer (50 mM Tris 7.4, 200 mM NaCl 10 mM CaCl2). Gelatinolytic activity was visualized by staining the gels with 0.5% Coomassie blue.

EXAMPLE 5
Tumor Growth Assay

Primary tumors were grown on CAMs of 9-day embryos by implantation 5x10$^6$ CS-1 cells and incubation for 7 days. At this point, 50 mg sections of these tumors were subcultured onto fresh 9-day CAMs and allowed to implant for 24 hours before a single intravenous (IV) injection with 100 μl of 100 μM of test compounds in Hank's Balanced Saline Solution (HBSS). Buffer alone was used as control. Tumors were incubated for a total of 10 days, harvested and trimmed free of excess stromal tissue before determining wet weight and processing for histology.

EXAMPLE 6
Immunofluorescence Assays

Snap-frozen CS-1 tumor sections were fixed with 4% paraformaldehyde and permeablized with 0.1% Triton X-100. Sections were blocked with 5% bovine serum albumin (BSA) in phosphate buffered saline (PBS) prior to staining with an anti-vWF pAb and visualization with an Alexa 568-conjugated anti-rabbit secondary antibody. Samples were analyzed on a MRC1024 confocal microscope (BioRad, Hercules, Calif.). Blood vessel density was quantitated with a 20×objective on four fields per section and four tumors per condition.

EXAMPLE 7
(S)-Methyl 6-(((tert-butyloxy)carbonyl)amino)-2-((4-trifluoromethyl)-benzyloxycarbonyl)hexanoate(2)

A solution of N,N'-disuccinimidyl carbonate (5.38 g, 21 mmol) in acetonitrile (150 mL) was treated with 4-(trifluoromethyl)benzyl alcohol (2.87 mL, 21 mmol) and Et$_3$N (5.8 mL, 42 mmol) and stirred at 25° C. After 3 h, the reaction mixture was added to a flask containing N-ε-BOC-lysine methyl ester (4.2 g, 14 mmol) in acetonitrile and stirred for an additional 3 h. The solvent was evaporated and the residue dissolved in $CH_2Cl_2$ (250 mL) and washed with 10% aqueous HCl (2×200 mL) and saturated aqueous NaHCO$_3$, (200 mL). Flash chromatography (SiO$_2$, 3:1 $CH_2Cl_2$/EtOAc) provided 6.4 g (99%) of 2 as a pale yellow oil: $[\alpha]_D^{25}$ -8.9 (c 5.6, $CH_3OH$); $^1$H NMR (CDCl$_3$, 400 MHz) δ 7.57 (d, J=8.1 Hz, 2H), 7.39 (d, J=8.1 Hz, 2H), 5.70 (d, J=7.9 Hz, 1H), 5.13 (m, 2H), 4.71 (m, 1H), 4.28 (m, 1H), 3.67 (s, 3H), 3.03 (m, 2H), 1.78 (m, 1H), 1.64, (m, 1H) 1.46–1.32 (m, 4H) 1.35 (s, 9H); $^{13}$C NMR (CDCl$_3$, 100 MHz) δ 172.9, 156.2, 155.8, 140.4, 130.1 (q, J=32.0 Hz), 127.8, 125.3, 122.9 (q, J=270.0 Hz), 79.05, 65.8, 53.7, 52.3, 39.8, 31.7, 29.5, 28.4, 22.2; IR (film) $\upsilon_{max}$ 3357, 2952, 1790, 1745, 1524 cm$^{-1}$; FABHRMS (NBA-NaI) m/z 463.2044 (M+H$^+$, $C_{21}H_{29}F_3N_2O_6$ requires 463.2056).

EXAMPLE 8
(S)-Methyl 6-[2-(((tert-butyloxy)carbonyl)amino) acetamido]-2-[(4-trifluoromethyl)benzyloxycarbonyl] hexanoate (3)

A solution of Compound 2 (2.7 g, 5.8 mmol) in $CH_2Cl_2$ (3 mL) was treated with 4N HCl-dioxane (10 mL) and stirred for 20 min at 25° C. Solvent and excess acid were removed under reduced pressure, and the crude hydrochloride salt was dissolved in DMF (50 mL), treated with N-((tert-butyloxy)carbonyl)glycine (1.0 g, 5.8 mmol), 1-(3-(dimethylamino)propyl)-3-ethylcarbodiimide hydrochloride (EDCI) (1.2 g, 6.4 mmol) and i-Pr$_2$NEt (2.0 mL, 11.6 mmol) and stirred for 12 h at 25° C. The reaction mixture was diluted with EtOAc (400 mL) and washed with 10% aqueous HCl (3×250 mL) and saturated aqueous NaHCO$_3$ (250 mL), dried (Na$_2$SO$_4$) and evaporated to provide 2.89 g (96%) of Compound 3 as a white foamy solid: $[\alpha]_D^{25}$–10.4 (c 2.5, CH$_3$OH); $^1$H NMR (CDCl$_3$, 400 MHz) δ 7.59 (m, 2H), 7.45 (m, 2H), 6.19 (m, 1H), 5.51 (m, 1H), 5.13 (m, 2H), 4.32 (m, 2H), 3.74 (s, 3H), 3.73 (m, 2H), 3.26 (m, 2H), 1.81–1.39 (m, 6H) 1.44 (s, 9H); $^{13}$C NMR (CD$_3$OD, 100 MHz) δ 174.5, 172, 158.2, 158.1, 142.7, 130.8 (q, J=31.8 Hz), 128.8, 126.3, 125.5 (q, J=269.7 Hz), 80.5, 66.5, 55.3, 52.7, 44.6, 39.8, 32.1, 29.8, 24.0; IR (film) $\upsilon_{max}$ 3320, 2932, 1721, 1692, 1326 cm$^{-1}$; FABHRMS (NBA-CsI) m/z 652.1234 (M+Cs$^+$, C$_{23}$H$_{32}$F$_3$N$_3$O$_7$ requires 652.1247).

EXAMPLE 9
6-[2-(amino)acetamido]-2-[(4-trifluoromethyl)-benzyloxycarbonyl]hexanoate Hydrochloride (4)

A solution of Compound 3 (350 mg) in CH$_2$Cl$_2$ (2 mL) was treated with 4 N HCl-dioxane (5.0 mL) and stirred at 25° C. After 0.5 h, solvent and excess acid were removed under reduced pressure, providing 300 mg (99%) of Compound 4 as a pale yellow oil: $[\alpha]_D^{25}$–10.4 (c 3.0, CH$_3$OH); $^1$H NMR (CD$_3$OD, 400 MHz) δ 7.65 (d, J=8.2 Hz, 2H), 5.18 (d, J=13.3 Hz, 1H), 5.16 (d, J=13.3 Hz, 1H), 4.16 (m, 1H), 3.70 (s, 3H), 3.65 (s, 2H), 3.21 (t, J=7.1 Hz, 2H), 1.84 (m, 1H), 1.68 (m, 1H), 1.54 (m, 2H), 1.42 (m, 2H); $^{13}$C NMR (CD$_3$OD, 100 MHz) δ174.5, 167.1, 158.2, 142.8, 130.8 (q, J=31.8 Hz), 128.8, 126.3, 125.5 (q, J=270.1 Hz), 66.5, 55.4, 52.7, 41.5, 40.2, 32.1, 29.6, 24.1; IR (film) $\upsilon_{max}$3317, 2954, 1718, 1684, 1530, 1327 cm$^{-1}$; MALDIFTMS (DHB) m/z 442.1586 (M+Na$^+$, C$_{18}$H$_{24}$F$_3$N$_3$O$_5$ requires 442.1566).

EXAMPLE 10
N,N$^1$-Bis[(5-(S)-(methoxycarbonyl)-5[((4-trifluoromethyl)-benzyl oxycarbonyl)amino]pentyl)carboxamidomethyl] benzene-1,3dicarboxamide (5)

A solution of Compound 4 (2.05 g, 4.0 mmol) in CH$_2$Cl$_2$ (3.0 mL) was treated with 4 N HCl-dioxane (10.0 mL) and stirred for 20 min at 25° C. Solvent and excess acid were removed under reduced pressure, and the crude hydrochloride salt was suspended in DMF (40 mL) and treated with isophthaloyl dichloride (400 mg, 2.0 mmol), and i-Pr$_2$NEt (1.4 mL, 8.0 mmol) and stirred for 1 h at 25° C. The reaction mixture was diluted with EtOAc (400 mL) and washed with 10% aqueous HCl (3×200 mL) and 5% aqueous Na$_2$CO$_3$ (200 mL), dried (Na$_2$SO$_4$), and evaporated. Flash chromatography (SiO$_2$, 1:4.5:4.5 MeOH/CH$_2$Cl$_2$/EtOAc) provided 1.30 g (68%) of Compound 5 as a yellow powder: $[\alpha]_D^{25}$–6.4 (c 2.1, CH$_3$OH); $^1$H NMR (CDCl$_3$, 400 MHz) δ 8.29 (m, 2H), 8.11 (m, 2H), 7.87 (m, 4H), 7.53 (m, 2H), 7.39 (m, 2H), 6.88 (m, 2H), 5.94 (m, 2H), 5.08 (m, 4H), 4.30 (m, 2H), 4.01 (m, 4H), 3.70 (s, 6H), 3.23 (m, 4H), 1.77 (m, 2H), 1.67 (m, 2H), 1.51 (m, 4H), 1.37 (m, 4H); $^{13}$C NMR (CD$_3$OD, 100 MHz) δ 174.6, 171.5, 169.3, 158.3, 142.7, 135.3, 131.6, 30.8 (q, J=32.2), 129.8, 128.8, 127.6, 126.3, 125.5 (q, J=269.2), 66.5, 55.4, 52.7, 44.1, 40.0, 32.1, 29.8, 24.1; IR (film) $\upsilon_{max}$ 3305, 2951, 1716, 1651, 1538 cm$^{-1}$; FABHRMS (NBA-CsI) m/z 1101.2398 (M+Cs$^+$, C$_{44}$H$_{50}$F$_6$N$_6$O$_{12}$ requires 1101.2445).

EXAMPLE 11
N,N$^1$-Bis-[(5-(S)-carboxy-5-[((4-trifluoromethyl) benzyloxycarbonyl)amino]-pentyl)carboxamidomethyl] benzene-1,3-dicarboxamide (1)

A solution of Compound 5 (0.95 g. 0.98 mmol) in THF-MeOH (8.0 mL, 3:1) was treated with LiOH.H$_2$O (165 mg, 3.9 mmol) in H$_2$O (2.0 mL) and stirred at 0° C. After 2 h, the reaction was quenched by the addition of 10% aqueous HCl (20 mL) and the mixture was extracted with EtOAc (3×50 mL). The organic layers were combined and washed with saturated aqueous NaCl (50 mL), dried (Na$_2$SO$_4$) and evaporated to provide 0.86 g (93%) of Compound 1 as a white powder: $[\alpha]_D^{25}$–0.6 (c 3.2, CH$_3$OH); $^1$H NMR (CD$_3$OD, 400 MHz) δ 8.40 (m, 1H, 8.03 (dd, J=1.8, 7.8 Hz, 2H), 7.62 (d, J=8.1 Hz, 4H), 7.53 (t, J=6.1 Hz, 1H), 7.51 (d, J=8.1 Hz, 4H), 5.16 (d., J.=13.3 Hz, 2H), 5.13 (d, J=13.3 Hz, 2H), 4.12 (m, 2H), 4.00 (s, 4H), 3.22 (t, J=6.6 Hz, 4H), 1.85 (m, 2H), 1.70 (m, 2H), 1.55 (m, 4H, 1.37 (m, 4H); $^{13}$C NMR (CD$_3$OD, 100 MHz) δ 175.9, 171.6, 169.4, 158.4, 135.4, 131.6, 30.5 (q, J=31.8), 129.8, 128.8, 127.7, 126.3, 125.5 (q. J=268.7); 66.5, 53.3, 44.2, 40.1, 32.2, 29.8, 24.2; IR (film) $\upsilon_{max}$ 3334, 2933, 1718, 1646, 1631, 1528 cm$^{-1}$; MALDIFTMS (DHB) m/z 963.2953 (M+Na$^+$, C$_{42}$H$_{46}$F$_6$N$_6$O$_{12}$ requires 963.2976).

EXAMPLE 12
[$^{14}$C]-Compound (1)

A solution of [1-$^{14}$C]-glycine (American Radiolabeled Chemicals, 1.0 mCi, 55 mCi/mmol, 0.018 mmol) in 0.1 N HCl was transferred to a 4 mL vial and the solvent was removed under a stream of N$_2$. The resulting residue was treated with a solution of NaHCO$_3$, (4.6 mg, 0.054 mmol) in H$_2$O (0.25 mL) and a solution of di-tert-butyl dicarbonate (10.5 mL, 0.045 mmol) in THF (0.25 mL) and stirred at 25° C. After 12 h the solution had become homogeneous and was diluted with H$_2$O (1.0 mL) and washed with diethyl ether (2×1.0 mL). The aqueous solution was then acidified by the addition of 10% aqueous HCl (0.5 mL) and extracted with ethyl acetate (4×1.0 mL). The combined extracts were dried (Na$_2$SO$_4$) and evaporated under a stream of N$_2$ to provide 2.9 mg (92%) of [1-$^{14}$C]-N-BOC-glycine as a white film.

A solution of Compound 2 (50 mg, 0.11 mmol) in CH$_2$Cl$_2$(1 mL) was treated with 4 N HCl-dioxane (1 mL) and stirred for 1 h at 25° C. The reaction mixture was diluted with ethyl acetate (25 mL) and washed with 10% aqueous Na$_2$CO$_3$ (25 mL) and saturated aqueous NaCl (25 mL) dried (Na$_2$SO$_4$) and evaporated to provide the deprotected lysine as a colorless film. A portion of this free amine (4.5 mg, 0.013 mmol) in DMF (0.2 mL) was added to a 4 mL vial containing [1-$^{14}$C]-N-BOC-glycine (1.5 mg, 0.0085 mmol) and treated with i-Pr$_2$NEt (2 mL) and a solution of EDCI (5.0 mg, 0.026 mmol) in methylene chloride (0.1 mL) and stirred for 3 h at 25° C. The reaction mixture was diluted with EtOAc (2.0 mL) washed with 10% hydrochloric acid (3×1.0 mL), saturated aqueous Na$_2$CO$_3$ (1.0 mL) and saturated aqueous NaCl (1.0 mL), and evaporated. Preparative thin layer chromatography (PTLC) (SiO$_2$, EtOAc/CHCl$_3$ 1:1) provided 1.8 mg (41%) of [$^{14}$C]-Compound 3 as a white film.

A 4 mL vial containing [$^{14}$C]-Compound 3 (1.8 mg, 3.5 mmol) was treated with 4 N HCl-dioxane (0.25 mL) and the reaction stirred for 0.5 h at 25° C. Solvent and excess acid were evaporated under a stream of N$_2$ and the resulting crude hydrochloride salt was treated with isophthaloyl dichloride (355 mg 0.0018 mmol) in CH$_2$Cl$_2$ (0.1 mL), and i-Pr$_2$NEt (2.4 mL, 0.014 mmol) in CH$_2$Cl$_2$ (0.05 mL). After 3 h at 25° C., the reaction mixture was directly purified by PTLC (SiO$_2$, MeOH/CHCl$_3$/EtOAc 1:9:9) to provide 1.2 mg (71%) of [$^{14}$C]-Compound 5.

A solution of [$^{14}$C]-Compound 5 (1.2 mg) in THF-MeOH (0.2 mL, 1:1) was treated with a solution of LiOH.H$_2$O (0.4 mg) in H$_2$O (0.05 mL) at 0° C. and stirred for 1 H. The reaction mixture was diluted with methanol (1.0 mL) and treated with Dowex 50WX-8 acid cation exchange resin (200 mg) and stirred for 1 min. The mixture was then filtered through cotton wool and the filtrate evaporated to provide 1.1 mg (94%) of [$^{14}$C]-Compound 1 relative activity approximately 110 mCi/mmol. This compound and all its synthetic intermediates were identical by thin layer chromatography (TLC) comparison to the corresponding unlabeled material.

EXAMPLE 13

(S)-Methyl 6-[2-(benzoylamino)acetamido]-2-[(4-trifluoromethyl)benzyloxycarbonyl)hexanoate (6)

A solution of Compound 3 (44 mg, 0.085 mmol) in CH$_2$Cl$_2$ (1.0 mL) was treated with 4 N HCl-dioxane (1.0 mL) and stirred for 1 h at 25° C. Solvent and excess acid were removed under a stream of N$_2$, and the crude by hydrochloride salt was suspended in CH$_2$Cl$_2$ (0.8 mL) and treated with i-Pr$_2$NEt (30 μL, 017 mmol) and benzoyl chloride (11 μL, 0.094 mmol) and stirred for 25° C. After 2 h the reaction mixture was directly purified by flash chromatography (SiO$_2$, 1:9:9 MeOH/CH$_2$Cl$_2$/EtOAc) to afford 40 mg (90%) of Compound 6 as a white powder: [α]$_D^{25}$–27 (c 0.70, CHCl$_3$); $^1$H NMR (CD$_3$OD, 400 MHz) δ 7.86 (m, 2H), 7.64 (m, 2H), 7.53 (m, 3H), 7.45 (m, 2H), 5.16 (m, 2H), 5.16 (dd, J=7.3, 3.8 Hz, 1H), 3.69 (s, 3H), 3.21 (t, J=5.6 Hz, 2H), 1.81 (m, 1H), 1.69 (m, 1H), 1.53 (m 2H), 1.42 (m, 2H); $^{13}$C NMR (CDCl$_3$, 100 MHz) δ 172.8, 169.5, 168.4, 156.3, 142.3, 132.9, 131.4, 129.4 (q, J=32.2 Hz), 128.0, 127.1, 126.7, 126.3 (q, J–269.0 Hz), 124.8, 65.1, 53.6, 51.6, 42.6, 38.4, 30.6, 28.1, 22.2; IR (film) υ$_{max}$ 3303, 2923, 1713, 1651, 1533 cm$^{-1}$; FABHRMS (NBA-CsI) m/z 656.0961 (M+Cs, C$_{25}$H$_{25}$F$_3$N$_3$O$_6$ requires 656.0985).

EXAMPLE 14

(S)-6-[2-(Benzoylamino)acetamido]-2-(4-trifluoromethyl) benzyloxycarbonyl]hexanoic Acid (7)

A solution of Compound 6 (17 mg, 0.032 mmol) in THF-MeOH (0.4 mL, 3:1) was treated with LiOH.H$_2$O (2.0 mg, 0.49 mmol) dissolved in H$_2$O (0.1 mL), and stirred for 2 h at 0° C. The reaction mixture was quenched by the addition of concentrated aqueous HCl (5 μL), diluted with EtOAc (30 mL) and washed with water (2×15 mL). Drying (Na$_2$SO$_4$) and evaporation provided 14.5 mg (88%) of Compound 7 as a white powder: [α]$_D^{25}$+2.2 (c 0.6, CH$_3$OH); $^1$H NMR (CD$_3$OD, 400 MHz) δ 7.86 (d, J=7.2 Hz, 2H), 7.62 (d, J=8.2 Hz, 2H), 7.54 (d, J=8.2 Hz, 2H), 7.53 (m, 1H), 7.43 (m, 2H), 5.17 (d, J=13.2 Hz, 1H), 5.14 (d, J–13.2 Hz, 1H0, 4.14 (m, 1H), 4.04 (s, 2H), 3.25 (m, 2H), 1.88 (m, 1H), 1.71 (m, 1H), 1.52 (m, 2H), 1.44 (m, 2H); $^{13}$C NMR (CD$_3$OD, 125 MHz) δ 175.9, 171.7, 170.5, 158.4, 142.9, 135.1, 132.9, 130.9 (q, J=32.4 Hz), 129.5, 128.9, 128.5, 126.3, 125.7 (q, J–269.0 Hz), 66.5, 55.4, 44.1, 40.1, 32.3, 29.9, 24.2; IR (film) υ$_{max}$ 3318, 2935, 1713, 1644, 1538, 1326 cm$^{-1}$; MALDIFTMS m/z 532.1672 (M+Na$^+$, C$_{24}$H$_{26}$F$_3$N$_3$O$_6$ requires 532.1671).

EXAMPLE 15

(S)-Methyl 6-[2-[(2-((carboxymethyl)methoxy)acetamido] acetamido]-2-[(4-trifluoromethyl)benzyloxycarbonyl] hexanoate (8)

A solution of Compound 3 (57 mg, 0.11 mmol) in CH$_2$Cl$_2$ (1 mL) was treated with 4 N HCl-dioxane (2 mL) and stirred for 1 h at 25° C. Solvent and excess acid were removed under a stream of N$_2$, and the residue was dissolved in DMF (1 mL) and treated with diglycolic acid (16 mg, 0.12 mmol), EDCI (23 mg, 0.12 mmol) and i-Pr$_2$NEt (42 μL, 0.24 mmol) and stirred at 25° C. After 4 h, the reaction mixture was poured into a separatory funnel containing EtOAc (50 mL) and washed with 10% aqueous HCl (3×30 mL) and saturated aqueous NaCl (30 mL), dried (Na$_2$SO$_4$) and evaporated to afford 45 mg (77%) of monoacid Compound 8 as a white solid: [α]$_D^{25}$–7.5 (c 1.8, CH$_3$OH); $^1$H NMR (CD$_3$OD, 400 MHz) δ 7.65 (d, J=5.2 Hz, 2H), 7.54 (d, J=5.3 Hz, 2H), 5.18 (d, J=9.0 Hz, 1H), 5.15 (d, J=9.0 Hz, 1H), 4.42 (s, 2H), 4.16 (m, 1H), 4.11 (s, 2H), 3.87 (s, 2H), 3.70 (s, 3H), 3.20 (t, J=4.5 Hz, 2H), 1.81 (m, 1H), 1.68 (m, 1H), 1.53 (m, 2H), 1.39 (m, 2H); $^{13}$C NMR (CD$_3$OD, 100 MHz) δ 174.5, 173.7, 172.5, 171.2, 158.2, 142.6, 130.9 (q, J=33.2 Hz), 128.2, 126.2, 125.4 (q, J=270.1 Hz), 71.3, 69.0, 66.5, 55.3, 52.7, 42.9, 39.9, 32.0, 29.7, 23.9; IR (film) υ$_{max}$ 3315, 2931, 1725, 1661, 1538, 1326 cm$^{-1}$; MALDIFTMS m/z 558.1686 (M+Na$^+$, C$_{22}$H$_{23}$F$_3$N$_3$O$_9$ requires 558.1673).

EXAMPLE 16

(S)-Methyl 2-(benzoylamino)-6-(((tert-butyloxy)carbonyl) amino)hexanoate (9)

A solution of N-ε-BOC-lysine methyl ester hydrochloride (5.05 g, 17 mmol) in CH$_2$Cl$_2$ (100 mL) was treated with benzoyl chloride (2.0 mL, 17 mmol) and i-Pr$_2$NEt (5.9 mL, 34 mmol) and stirred at 25° C. After 1 h the reaction mixture was washed with 10% aqueous HCl (100 mL), dried (Na$_2$SO$_4$) and evaporated to a white powder which was crystallized from CH$_2$Cl$_2$-hexanes to afford 4.8 g (78%) of Compound 9 as a white crystalline solid with mp 108–109° C.; [α]$_D^{25}$–13.2 (c 5.8), CH$_3$OH); $^1$H NMR (DMSO-d$_6$, 400 MHz) δ 8.72 J=7.4 Hz, 1H), 7.89 (m, 2H), 7.55 (m, 1H), 7.48 (m, 2H), 6.88 (t, J–5.2 Hz, 1H), 4.42 (m, 1H), 3.64 (s, 3H), 2.93 (m, 2H), 1.81 (m, 2H), 1.41 (m, 4H), 1.37 (s, 9H); $^{13}$C NMR (DMSO-d$_6$, 100 MHz) δ 172.9, 166.7, 155.6, 133.8, 131.5, 128.3, 127.6, 77.4, 52.8, 51.9, 40.8, 30.2, 29.2, 28.3, 23.2; IR (film) υ$_{max}$ 3335, 2933, 1740, 1690, 1647, 1534 cm$^{-1}$; MALDIFTMS (DHB) m/z 387.1895 (M+Na$^+$, C$_{19}$H$_{25}$N$_2$O$_5$ requires 387.1890).

EXAMPLE 17

(S)-Methyl 2-(benzoylamino)-6-[2-(((tert-butyloxy) carbonyl)amino]-acetamido)hexanoate (10)

A solution of Compound 9 (4.4 g, 12.1 mmol) in CH$_2$Cl (5.0 mL) was treated with 4 N HCl-dioxane (10.0 mL) and stirred for 3 h at 25° C. Solvent and excess acid were removed under reduced pressure, and the residue was dissolved in DMF (150 mL) and treated with N-((tert-butyloxy) carbonyl)glycine (2.2 g, 12.1 mmol), PyBrOP (7.0 g, 15 mmol), and i-Pr$_2$NEt (8.4 mL, 48.4 mmol) and stirred at 25° C. After 12 h the reaction mixture was diluted with EtOAc (500 mL) and washed with 10% aqueous HCl (3×250 mL), 5% aqueous Na$_2$CO$_3$ (250 mL) and saturated aqueous NaCl (250 mL), dried Na$_2$SO$_4$) and evaporated. Flash Chromatography (SiO$_2$, EtOAc) provided 4.6 (90%) of Compound 10 as colorless oil: [α]$_D^{25}$–10.3 (c 0.30, CH$_3$OH); $^1$H NMR (CDCl$_3$, 400 MHz) δ 7.84 (m, 2H), 7.51 (m, 1H), 7.44 (m, 2H), 6.91 (d, J–7.6 Hz, 1H), 6.35 (brt, J–5.3 Hz, 1H), 5.22 (m, 1H), 4.76 (m, 1H), 3.76 (s, 3H), 3.70 (brt, J–6.3 Hz, 4H), 3.26 (m, 2H), 1.95 (m, 1H), 1.84 (m, 1H), 1.57–1.30 (m, 4H), 1.41 (s, 9H); $^{13}$C NMR (CDCl$_3$, 100 MHz) δ 173.0, 169.7, 167.3, 156.5, 133.7, 131.8, 128.6, 127.2, 81.8, 52.5, 52.3, 44.3, 38.7, 32.0, 28.9, 28.3, 22.4; IR (film) ν$_{max}$ 3318, 2954, 1718, 1647, 1535, 1491 cm$^{-1}$; MALDIFTMS m/z 444.2108 (M+Na$^+$, C$_{21}$H$_{31}$N$_3$O$_6$ requires 444.2110).

EXAMPLE 18
N,N'-Bis[N-(-5-(S)-((benzoyl)amino)-5-(methoxycarbonyl)pentyl)carboxamidomethyl]benzene-1,3-dicarboxamide (11)

A solution of Compound 10 (4.4 g, 10.4 mmol) in CH$_2$Cl$_2$ (3 mL) was treated with 4.0 N HCl-dioxane (20 mL) and stirred for 1H at 25° C. Solvent and excess acid were removed under reduced pressure, and the residue dissolved in CH$_2$Cl$_2$ (50 mL) and treated with Et$_2$N (5.8 mL, 42 mmol) and isophthaloyl dichloride (1.06 g, 5.2 mmol) and stirred at 25° C. After 16 h, the reaction mixture was washed with 10% aqueous HCl (50 mL) and evaporated to a yellow oil. Flash chromatography (SiO$_2$, 5:5:2 EtOAc/CH$_2$Cl$_2$/MeOH) afforded 2.5 g (62%) of Compound 11 as a white foamy solid: [α]$_D^{25}$–8.0 (c 4.8, CH$_3$OH); $^1$H NMR (CD$_3$OD, 500 MHz) δ 8.37 (s, 1H), 8.00 (m, 2H) 7.84 (m, 4H), 7.52 (m, 3H), 7.44 (m, 4H), 4.58 (m, 2H), 3.99 (two s, 4H); 3.72 (s, 6H), 3.22 (m, 4H), 1.99–1.83 (m, 4H), 1.59–1.40 (m, 8H); $^{13}$C NMR (CD$_3$OD, 100 MHz) δ 174.2, 171.5, 170.2, 169.0, 135.0, 134.8, 132.8, 131.5, 129.4, 128.4, 127.6, 54.3, 52.7, 44.2, 40.1, 31.7, 29.8, 24.3; IR (film) ν$_{max}$ 3304, 2950, 1738, 1650, 1644, 1538 cm$^{-1}$; , MALDIFTMS m/z 795.3332 (M+Na$^+$, C$_{40}$H$_{45}$N$_6$O$_{10}$ requires 795.3330).

EXAMPLE 19
N,N'-Bis-[N-(-5-(S)-((benzoyl)amino)-5-(carboxy)pentyl)carboxamidomethyl]benzene-1,3-dicarboxamide (12)

A solution of Compound 11 (1.1 g, 1.4 mmol) in MeOH-THF (20 mL, 1:1) was treated with LiOH.H$_2$O (240 mg, 5.7 mmol) dissolved in H$_2$O (10 mL) and stirred for 1 h at 0° C. After 1 h, the reaction solvent was evaporated and the residue redissolved in H$_2$O (20 mL) and cooled to 0° C. Concentrated aqueous HCl (0.47 mL, 5.7 mmol HCl) was added and the solid which precipitated was filtered and washed with water (50 mL to afford 0.78 g (73%) of Compound 12 as a white powder: [α]$_D^{25}$–2.6 (c 0.35, CH$_3$OH); $^1$H NMR (CD$_3$OD, 400 MHZ) δ 8.38 (m, 1H), 8.02 (m, 2H), 7.84 (m, 4H), 7.55–7.48 (m, 3H), 7.42 (m, 4H), 4.56 (m, 2H), 4.00 and 3.99 (two s, 4H), 3.26 (m, 4H), 1.99–1.83 (m, 4H), 1.63–1.45 (m, 8H); $^{13}$C NMR (CD$_3$OD, 100 MHz) δ 175.5, 171.9, 170.4, 169.2, 135.0, 134.9, 132.8, 131.7, 129.8, 129.5, 128.5, 127.7, 54.4, 44.0, 40.2, 31.7, 29.6, 24.3; IR (film) υ$_{max}$ 3280, 2923, 1718, 1641, 1536 cm$^{-1}$; MALDIFTMS (DHB) m/z 767.3005 (M+Na$^+$, C$_{38}$H$_{44}$N$_6$O$_{10}$ requires 767.3017).

Results and Discussion

Figure 2:
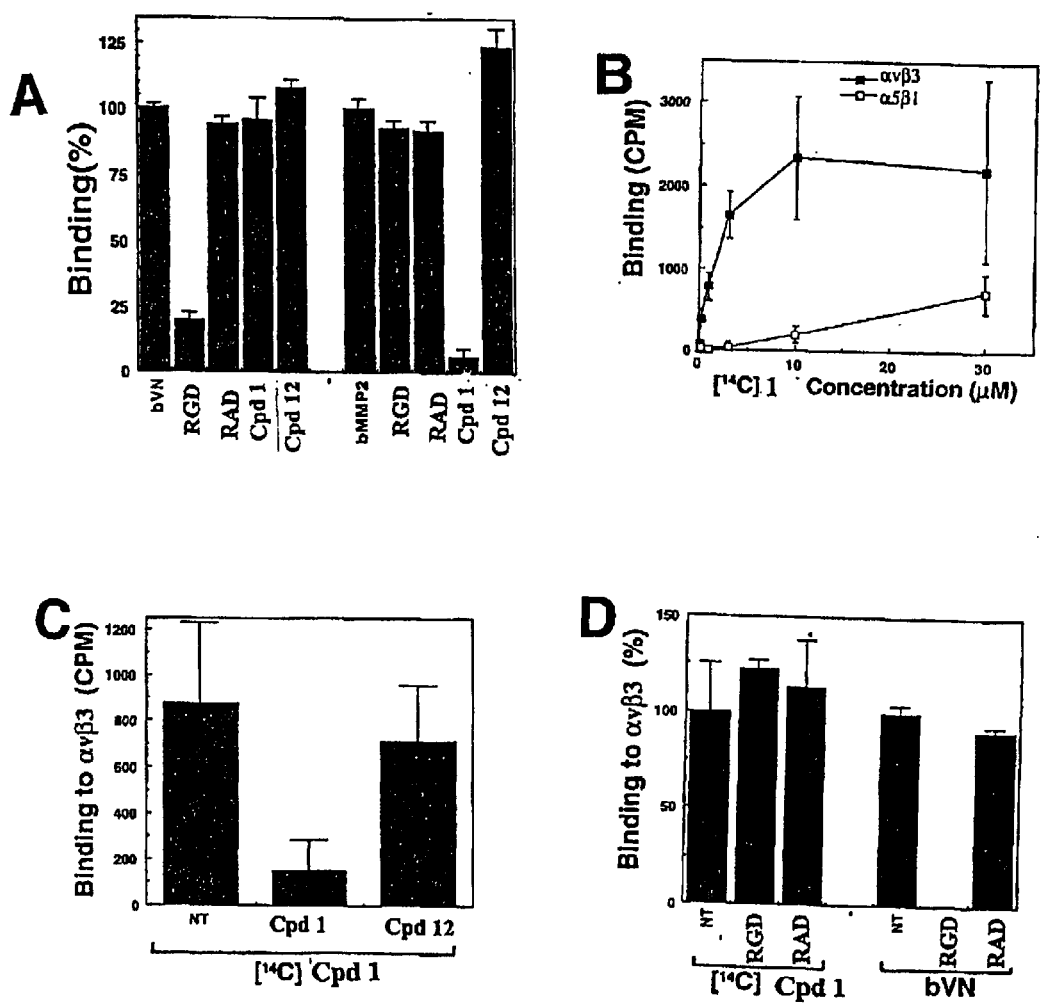
FIG. 2A graphically illustrates the effect of inhibitor compounds of Formula (I) on MMP2 interaction with integrin $\alpha_v\beta_3$ in a solid phase binding assay.
FIG. 2B illustrates the binding of compounds of Formula (I) on with integrin $\alpha_v\beta_3$ and $\alpha_5\beta_1$.
FIG. 2C compares the effect of a compound of the present invention with a control compound on binding to $\alpha_v\beta_3$.
FIG. 2D compares the effect of amino acid residues RGD on binding of a present compound to $\alpha_v\beta_3$ with the effect of RGD on binding of bVN to $\alpha_v\beta_3$.

Compound 1 disrupts the RGD-independent interaction between integrin α$_v$β$_3$ and MMP2. The recent observation that the carboxy-terminal hemopexin-like domain of MMP2 can interfere with MMP2 binding to integrin α$_v$β$_3$ and thus block angiogenesis prompted us to search for organic inhibitors of this interaction, which might be more amenable to therapeutic administration. To identify a specific inhibitor of the binding interaction between MMP2 and integrin α$_v$β$_3$, solid phase receptor binding assays were performed with immobilized integrins and biotinylated MMP2. The binding of purified MMP2 was found to be entirely RGD-independent in this system, as evidenced by the lack of effect of cRGDfV on MMP2 binding to integrin α$_v$β$_3$, even though this peptide inhibited the interaction of α$_v$β$_3$ with its extracellular matrix ligand, vitronectin (VN; FIG. 2A). Importantly, the binding of MMP2, but not that of VN, was completely abrogated by Compound 1, demonstrating the specificity of Compound 1 for the interaction between MMP2 and α$_v$β$_3$. Furthermore, the binding between MMP2 and tissue inhibitor of metalloproteinase 2 (TIMP2) was not inhibited by Compound 1, supporting the contention that the effect of this Compound 1 is restricted to the binding interaction between MMP2 and integrin α$_v$β$_3$, and demonstrating a distinction between the binding sites for the MMP2 PEX domain on TIMP2 and integrin α$_v$β$_3$. It is important to note that neither the control compound nor the control peptide cRADfV interfered with MMP2 binding to integrin α$_v$β$_3$ (FIG. 2A).

Compound 1 binds directly to integrin α$_v$β$_3$ and not to MMP2. To further address the mechanism of action of Compound 1, additional solid phase receptor binding assays were performed with immobilized α$_v$β$_3$ and [$^{14}$C]-labeled Compound 1, or biotinylated VN as a control. As can be seen in FIG. 2B, Compound 1 bound directly to integrin α$_v$β$_3$ in a solid phase receptor binding assay. This interaction was dose-dependent, saturable and specific, demonstrating minimal interaction of Compound 1 with the unrelated control integrin α5β$_1$ (FIG. 2B). Indeed, negligible binding to integrin α5β$_1$ was observed at higher concentrations of compound (data not shown). In addition, no binding of Compound 1 was observed when MMP2 was coated on the microtiter well (data not shown), suggesting that the effects observed in the MMP2/integrin α$_v$β$_3$ binding assay are due to Compound 1 binding to integrin α$_v$β$_3$. Importantly, this interaction was inhibited by the presence of a 25-fold molar excess of unlabeled Compound 1, but not the related control compound 12 (FIG. 2C). Furthermore, Compound 1 bound to integrin α$_v$β$_3$ in an RGD-independent manner, as demonstrated by the inability of the cRGDfV peptide to inhibit the interaction of radiolabeled Compound 1 with integrin α$_v$β$_3$, even as cRGDfV completely abolished the binding of bVN to the immobilized integrin in the same system (FIG. 2D). The control peptide cRADfV is shown as a control for the specificity of the binding inhibition. Thus, Compound 1 binding to α$_v$β$_3$ exhibits comparable specificity, selectivity and lack of susceptibility to RGD inhibition to that of MMP2.

Interestingly, Compound 6, the compound of Formula (II) where A is hydrogen, n is 0, X$^1$ is p-trifluoromethyl and R$^1$ is methyl, was slightly less active than Compound 1 in the solid phase binding assay, whereas Compound 8, which lacks the phenyl group coupled to the glycine unit was inactive. This result demonstrates that the phenyl ring is an essential feature for inhibition activity for the inhibitor compounds of Formula (II), and further demonstrates that at least one substituted glycyl lysine unit is necessary for the antiangiogenic activity of this class of inhibitors.

Figure 3:
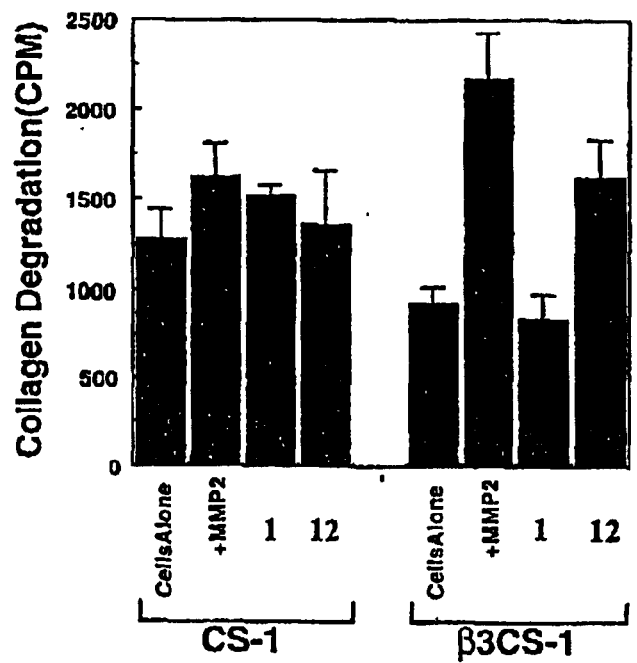
FIG. 3A graphically illustrates proteinase activity in $\beta_3$ positive cells and in $\beta_3$ negative cells.
FIG. 3B illustrates MMP2 binding in $\beta_3$ positive cells and $\beta_3$ negative cells.
Figure 3:
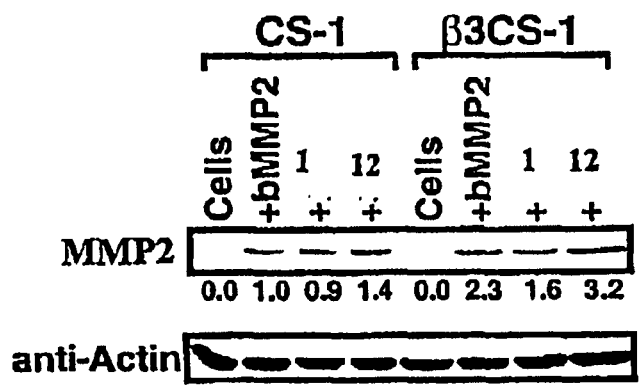

Cell-mediated collagen IV degradation via MMP2 is blocked by Compound 1. Prevention of MMP2 binding to integrin $\alpha_v\beta_3$ on melanoma cells was shown previously to inhibit cell-mediated collagen IV degradation in an $\alpha_v\beta_3$-dependent manner. Therefore, we assessed whether melanoma cells expressing or lacking $\alpha_v\beta_3$ could utilize activated MMP2 to degrade immobilized [$^3$H]collagen IV. Importantly, neither cell produces detectable quantities of MMP2 endogenously. While both cell types were capable of some level of basal collagen degradation, only the $\beta_3$-transfected CS-1 cells were able to utilize the exogeneous MMP2, demonstrating significantly more release of substratum radioactivity into the culture medium after preincubation with purified MMP2 (FIG. 3A). This enhanced substrate degradation in response to treatment with MMP2 was specifically abolished by inclusion of Compound 1, while Compound 12 had a negligible effect (FIG. 3A). Significantly, the effect of Compound 1 on cell-mediated collagen degradation was not due to a direct inhibition of MMP2 activity, as purified active MMP2 in the absence of cells was still able to degrade the immobilized [$^3$H]collagen IV irrespective of the presence or absence of either Compound 1 or Compound 12. To demonstrate that the reduced cell-mediated collagen degradation observed in FIG. 3A was the result of inhibition of MMP2 interaction with integrin $\alpha_v\beta_3$ by Compound 1 on the cell surface, CS-1 cells and their $\alpha_v\beta_3$-bearing counterpart were examined in a biotinylated MMP2 binding assay. As expected, the $\beta_3$-negative CS-1 cells were capable of binding some level of MMP2, however their capacity to do so was not diminished by the presence of either compound (FIG. 3B). In contrast, $\beta_3$CS-1 cells bound significantly greater quantities of MMP2, and this enhanced MMP2 binding was specifically suppressed by Compound 1. In fact, when corrected for the loading of the lanes as demonstrated by staining with an anti-actin mAb, Compound 1 effectively reduced the binding of MMP2 to the $\beta_3$CS-1 cells to the level observed in the absence $\alpha_v\beta_3$ (i.e. parental CS-1 cells) (FIG. 3B, lane 2).

Figure 4:
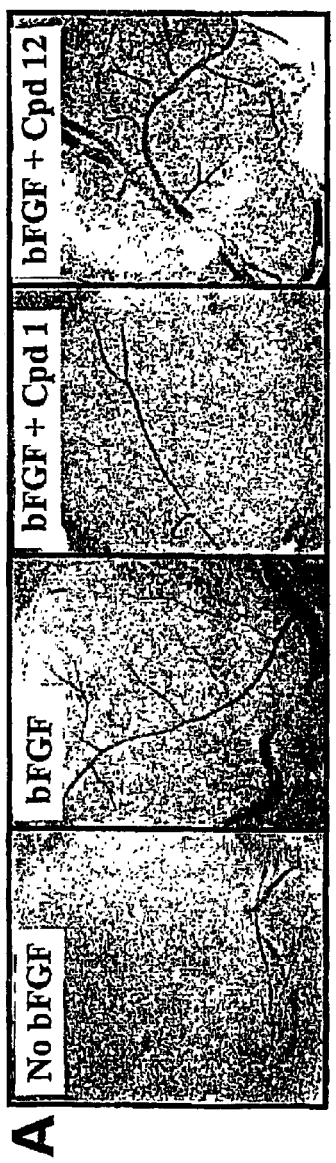
FIG. 4A is a microscopic depiction of angiogenesis inhibition in Chick CAM tissue.
FIG. 4B is a graphical illustration of angiogenesis inhibition in Chick CAM tissue.
FIG. 4C depicts the levels of MMP2 in treated and untreated cells.
Figure 4:
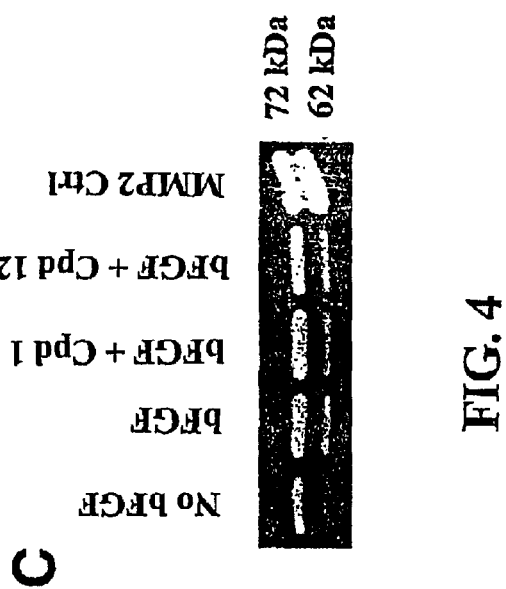
Figure 4:
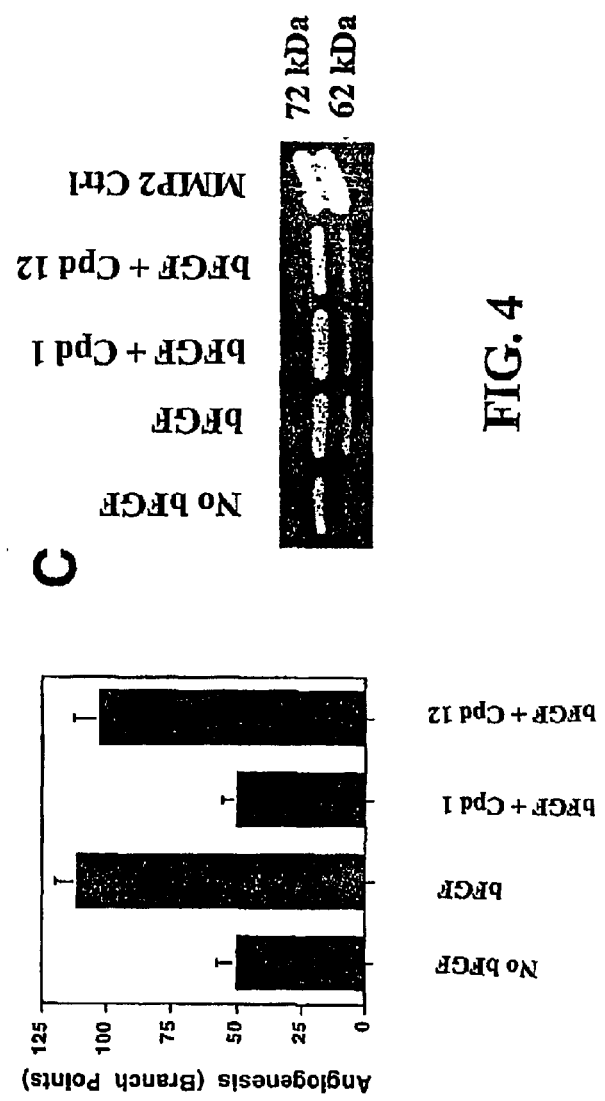

Compound 1 disrupts angiogenesis in vivo without suppressing MMP2 activation. Suppression of $\alpha_v\beta_3$/MMP2 interaction by exogenously applied recombinant MMP2 PEX domain was shown previously to impair angiogenesis in animal models. Therefore, we examined the effects of Compound 1 on growth factor-induced angiogenesis on the 10 day old chick CAM. Application of Compound 1 to CAMs that had been stimulated with basic fibroblast growth factor (bFGF) almost completely abolished the development of new blood vessels in response to this stimuli (FIGS. 4A & 4B), while the control Compound 12 was ineffective in this regard. Importantly, the abrogation of angiogenic infiltration in response to Compound 1 was not associated with suppression of MMP2 activation since equivalent levels of active MMP2 (62 kDa) were detected in CAM tissues from treated and untreated embryos (FIG. 4C). This is in stark contrast to the effect of exogenous MMP2 PEX domain, which suppressed MMP2 activation in this system. These data are consistent with the notion that Compound 1 specifically interferes with the binding of MMP2 to integrin $\alpha_v\beta_3$, without impacting the activation of MMP2 directly. Indeed, the overall levels of MMP2 observed in the CAM lysates were unaffected by Compound 1 treatment as well, ruling out a potential effect on the expression level of MMP2 in the angiogenic tissues (FIG. 4C). These results suggest that the antiangiogenic effects of Compound 1 are likely due to the suppression of MMP2 binding to integrin $\alpha_v\beta_3$ on the cell surface as demonstrated in FIG. 3B. These data also indicate that MMP2 which is fully activated is not utilized for angiogenesis in this system unless coupled to integrin $\alpha_v\beta_3$ on the cell surface.

Figure 5:
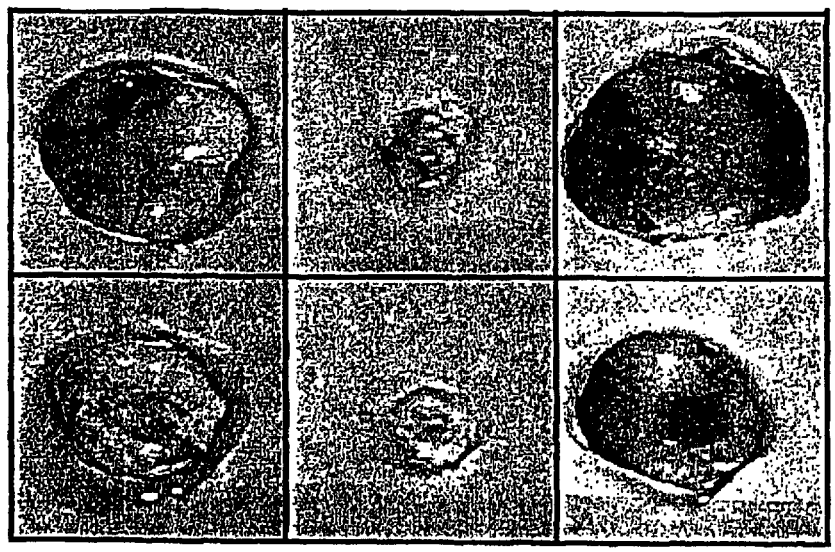
FIG. 5A is a microscopic depiction of tumor growth and vasculature in Chick CAM tissue.
FIG. 5B is a microscopic depiction of blood vessel density in Chick CAM tissue.
FIG. 5C is graphical illustration of tumor weight in Chick CAM tissue.
FIG. 5D is a graphical illustration of vascularization in Chick CAM tissue.
Figure 5:
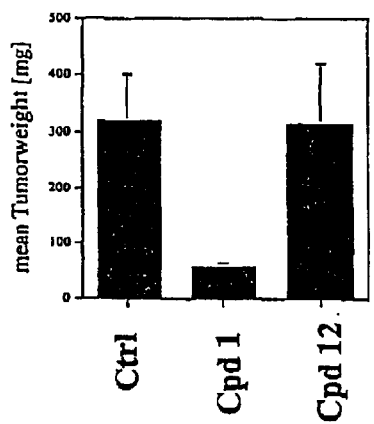
Figure 5:
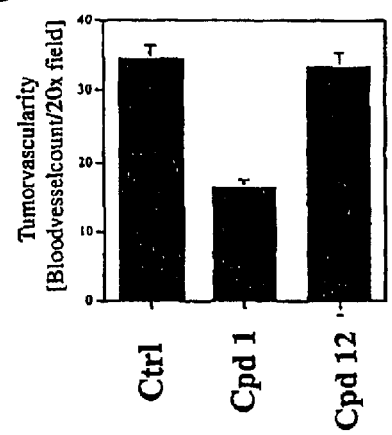

Compound 1 abrogates tumor growth in vivo. Disruption of angiogenesis has been shown to inhibit tumor growth in numerous systems. As a result, blocking the invasive properties of endothelial cells by inhibiting MMPs suppresses angiogenesis and tumor growth in animal models as well. In fact, a number of MMP inhibitors have shown promise as anti-angiogenic agents in man. Therefore, we assessed whether the inhibition of angiogenesis associated with blockade of MMP2/$\alpha_v\beta_3$ interactions observed in this study might be sufficient to suppress the growth of an $\alpha_v\beta_3$-negative tumor. The use of the $\alpha_v\beta_3$-negative tumor allowed the assessment of Compound 1's effect on vascular $\alpha_v\beta_3$ selectively. As shown in FIG. 5A, growth of transplanted $\alpha_v\beta_3$-negative CS-1 melanoma tumors on the chick CAM was significantly retarded by a single intravenous (IV) injection of Compound 1, as was tumor weight (FIG. 5B). It is likely that this effect was not due to a direct impact of Compound 1 on the tumor as the melanoma cells used in this assay lack integrin $\alpha_v\beta_3$. In fact, their growth in vitro is not affected by co-culture with the compound (data not shown). A gross reduction in the surface vasculature (FIG. 5A) as well as the overall blood vessel density (FIG. 5C) was evident in the tumors that had been treated with Compound 1. Importantly, this reduction in tumor vasculature was associated with significant cell death within the tumor mass, even as the control tumors showed a 6-fold increase in mass during the 10-day time frame of the assay.

The foregoing description and the Examples are to be taken as illustrative but not limiting. Still other variants within the spirit and scope of the present invention are possible and will readily present themselves to those skilled in the art.

We claim:

1. A compound of structure:

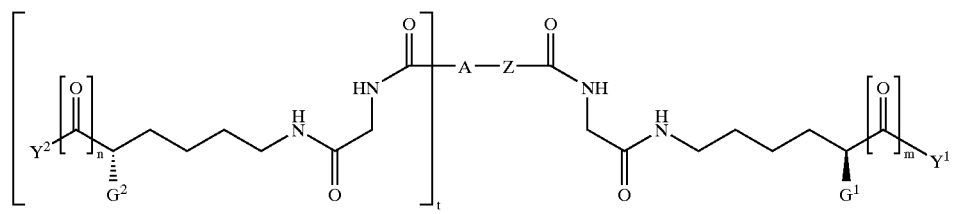

wherein $G^1$ and $G^2$ are each independently —NH—C(O)—O—$R^1$, —NH—C(O)—O—$(CH_2)_v$—$(C_6H_4)$—$X^1$, —NH—C(O)—NH—$(CH_2)_v$—$(C_6H_4)$—$X^1$, —O—C(O)—NH—$(CH_2)_v$—$(C_6H_4)$—$X^1$, —O—C(O)—O—$(CH_2)_v$—$(C_6H_4)$—$X^1$, or —NH—C(O)—$CH_2$—$(C_6H_4)$—$X^1$; $Y^1$ and $Y^2$ are each independently OH, $C_1$–$C_4$ alkyl, $C_1$–$C_4$ hydroxyalkyl, $C_1$–$C_4$ alkoxy, phenyl, benzyl, or —$NH_2$; $R^1$ is $C_1$–$C_4$ alkyl; $X^1$ is halo, nitro, $C_1$–$C_4$ alkyl, $C_1$–$C_4$ alkoxy, or $C_1$–$C_4$ perfluoroalkyl; Z is —C≡C—, —$C_6H_4$—, cis —CH=CH—, trans —CH=CH—, cis —$CH_2$—CH=CH—$CH_2$—, trans —$CH_2$—CH=CH—$CH_2$—, 1,4-naphthyl, cis-1,3-cyclohexyl, trans-1,3-cyclohexyl, cis-1,4-cyclohexyl, or trans-1,4-cyclohexyl; A is H or a covalent bond; m and n are each independently an integer having a value of 0 or 1; t is an integer having a value of 0 or 1; and v is an integer having a value of 1 or 2; with provisos that when A is H, t is 0; when A is a covalent bond, t is 1; when m is 0, $Y^1$ is $C_1$–$C_4$ hydroxyalkyl; and when n is 0, $Y^2$ is $C_1$–$C_4$ hydroxyalkyl.

2. The compound of claim 1 wherein $G^1$ and $G^2$ are —NH—C(O)—O—$(CH_2)_v$—$(C_6H_4)$—$X^1$, A is a covalent bond, and v is 1.

3. The compound of claim 2 wherein $X^1$ is trifluoromethyl.

4. The compound of claim 2 wherein $Y^1$ and $Y^2$ are OH, m is 1 and n is 1.

5. A compound of structure:

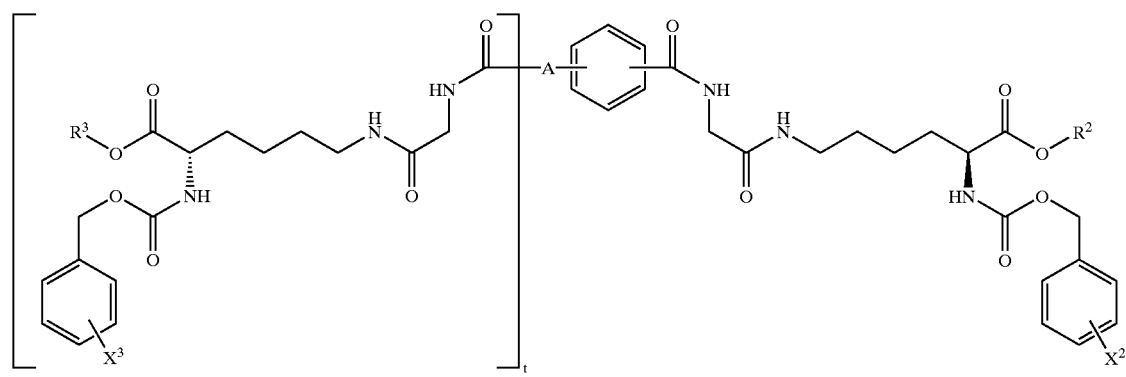

wherein $R^2$ and $R^3$ are each independently H, $C_1$–$C_4$ alkyl, phenyl or benzyl; $X^2$ and $X^3$ are each independently halo, nitro, $C_1$–$C_4$ alkoxy, $C_1$–$C_4$ alkyl, or $C_1$–$C_4$ perfluoroalkyl; A is H or a covalent bond; and t is an integer having a value of 0 or 1; with the proviso that when A is H, t is 0 and when A is a covalent bond, t is 1.

6. The compound of claim 5 wherein at least one of $X^2$ and $X^3$ is para-trifluoromethyl, and A is a covalent bond.

7. The compound of claim 5 wherein at least one of $R^2$ and $R^3$ is H, and A is a covalent bond.

8. The compound of claim 5 wherein at least one of $R^2$ and $R^3$ is methyl, and A is a covalent bond.

9. The compound of claim 5 wherein $X^2$ and $X^3$ are each para-trifluoromethyl, $R^2$ and $R^3$ are each methyl, and A is a covalent bond.

10. The compound of claim 5 wherein $R^2$ is H, and A is H.

11. The compound of claim 5 wherein $R^2$ is methyl, and A is H.

12. The compound of claim 5 wherein $X^2$ is para-trifluoromethyl, $R^1$ is H, and A is H.

13. The compound of structure:

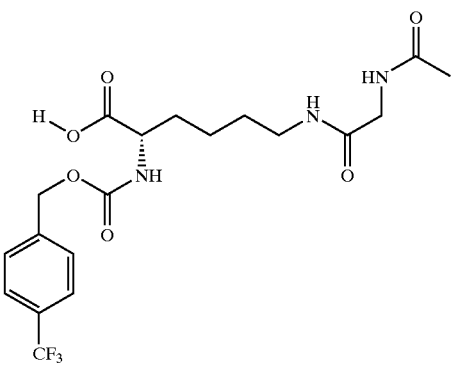

-continued

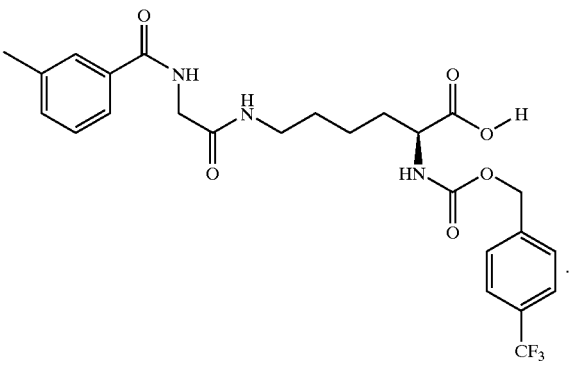

14. A pharmaceutical preparation comprising a compound of structure:

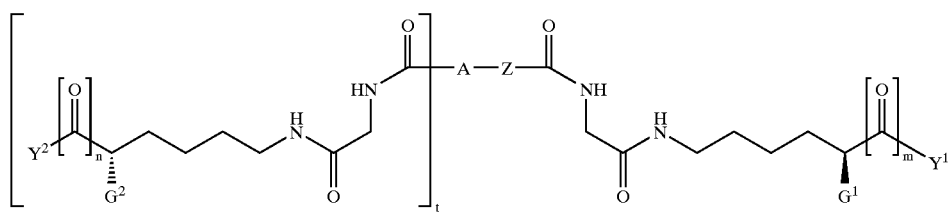

wherein $G^1$ and $G^2$ are each independently —NH—C(O)—O—$R^1$, —NH—C(O)—O—$(CH_2)_v$—$(C_6H_4)$—$X^1$, —NH—C(O)—NH—$(CH_2)_v$—$(C_6H_4)$—$X^1$, —O—C(O)—NH—$(CH_2)_v$—$(C_6H_4)$—$X^1$, —O—C(O)—O—$(CH_2)_v$—$(C_6H_4)$—$X^1$, or —NH—C(O)—$CH_2$—$(C_6H_4)$—$X^1$; $Y^1$ and $Y^2$ are each independently OH, $C_1$–$C_4$ alkyl, $C_1$–$C_4$ hydroxyalkyl, $C_1$–$C_4$ alkoxy, phenyl, benzyl, or —$NH_2$; $R^1$ is $C_1$–$C_4$ alkyl; $X^1$ is halo, nitro, $C_1$–$C_4$ alkyl, $C_1$–$C_4$ alkoxy, or $C_1$–$C_4$ perfluoroalkyl; Z is —C≡C—, —$C_6H_4$—, cis —CH=CH—, trans —CH=CH—, cis —$CH_2$—CH=CH—$CH_2$—, trans —$CH_2$—CH=CH—$CH_2$—, 1,4-naphthyl, cis-1,3-cyclohexyl, trans-1,3-cyclohexyl, cis-1,4-cyclohexyl, or trans-1,4-cyclohexyl; A is H or a covalent bond; m and n are each independently an integer having a value of 0 or 1; t is an integer having a value of 0 or 1; and v is an integer having a value of 1 or 2; with provisos that when A is H, t is 0; when A is a covalent bond, t is 1; when m is 0, $Y^1$ is $C_1$–$C_4$ hydroxyalkyl; and when n is 0, $Y^2$ is $C_1$–$C_4$ hydroxyalkyl; in a pharmaceutically acceptable carrier.

15. The pharmaceutical preparation of claim 14 wherein $G^1$ and $G^2$ are —NH—C(O)—O—$(CH_2)_v$—$(C_6H_4)$—$X^1$, A is a covalent bond, and v is 1.

16. The pharmaceutical preparation of claim 15 wherein $X^1$ is trifluoromethyl.

17. The pharmaceutical preparation of claim 15 wherein $Y^1$ and $Y^2$ are OH, m is 1 and n is 1.

18. The pharmaceutical preparation of claim 15 wherein $X^2$ is para-trifluoromethyl, $R^1$ is H, and A is H.

19. The pharmaceutical preparation comprising a compound of structure:

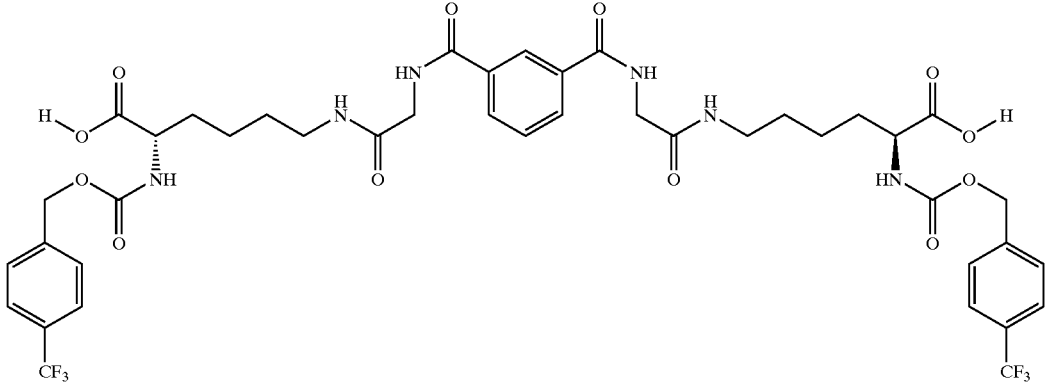

in a pharmaceutically acceptable carrier.

* * * * *

UNITED STATES PATENT AND TRADEMARK OFFICE
CERTIFICATE OF CORRECTION

PATENT NO. : 6,803,383 B2  
DATED : October 12, 2004  
INVENTOR(S) : Dale L. Boger et al.

Page 1 of 1

It is certified that error appears in the above-identified patent and that said Letters Patent is hereby corrected as shown below:

Column 1,  
Line 5, "March 2001" should be -- March 27, 2001 --.

Column 4,  
Lines 44-45, should be deleted.  
Line 46, "FIG. 5C" should be -- FIG. 5B --.  
Line 48, "FIG. 5D" should be -- FIG. 5C --.  
Lines 50-51, should be deleted.

Column 23,  
Line 33, "$[\alpha]_D^{25}$-27" should be -- $[\alpha]_D^{25}$-2.7 --.

Column 24,  
Line 44, "J=7.4 Hz, 1H)," should be -- (d, J=7.4 Hz, 1H), --.

Column 29,  
Line 3, "($_6H_4$)" should be -- ($C_6H_4$) --.

Signed and Sealed this

Sixteenth Day of August, 2005

JON W. DUDAS  
*Director of the United States Patent and Trademark Office*